(12) United States Patent
Armendariz Borunda et al.

(10) Patent No.: US 7,807,457 B2
(45) Date of Patent: Oct. 5, 2010

(54) RECOMBINANT VIRAL AND NON-VIRAL VECTORS CONTAINING THE HUMAN UROKINASE PLASMINOGEN ACTIVATOR GENE AND ITS UTILIZATION IN THE TREATMENT OF VARIOUS TYPES OF HEPATIC, RENAL, PULMONARY, PANCREATIC AND CARDIAC FIBROSIS AND HYPERTROPHIC SCARS

(75) Inventors: Juan Armendariz Borunda, Col. Prado Coapa (MX); Estuardo Aguilar Cordova, Col. Prado Coapa (MX)

(73) Assignee: TGT Laboratories, S.A. De C.V., Col. Prado Coapa (MX)

(*) Notice: Subject to any disclaimer, the term of this patent is extended or adjusted under 35 U.S.C. 154(b) by 327 days.

(21) Appl. No.: 10/432,989

(22) PCT Filed: Nov. 30, 2000

(86) PCT No.: PCT/MX00/00050

§ 371 (c)(1),
(2), (4) Date: Oct. 24, 2003

(87) PCT Pub. No.: WO02/44393

PCT Pub. Date: Jun. 6, 2002

(65) Prior Publication Data

US 2004/0097455 A1     May 20, 2004

(30) Foreign Application Priority Data

Dec. 28, 2000  (MX) .................................... 011713

(51) Int. Cl.
C12N 5/00     (2006.01)
C12N 15/00    (2006.01)
(52) U.S. Cl. .................................... 435/325; 435/320.1
(58) Field of Classification Search ................. 435/325, 435/320.1, 273, 375, 6, 91.1
See application file for complete search history.

(56) References Cited

U.S. PATENT DOCUMENTS

| | | | |
|---|---|---|---|
| 5,166,320 A | 11/1992 | Wu et al. ..................... 530/395 |
| 5,240,846 A | 8/1993 | Collins et al. ................ 435/371 |
| 5,521,291 A | 5/1996 | Curiel et al. ............. 530/391.7 |
| 5,547,932 A | 8/1996 | Curiel et al. ................. 435/456 |
| 5,559,099 A | 9/1996 | Wickham et al. .............. 514/44 |
| 5,585,362 A | 12/1996 | Wilson et al. ................. 514/44 |
| 5,670,488 A | 9/1997 | Gregory et al. ................ 514/44 |
| 5,712,136 A | 1/1998 | Wickham et al. ............ 435/456 |
| 5,756,086 A | 5/1998 | McClelland et al. ....... 424/93.2 |
| 5,770,442 A | 6/1998 | Wickham et al. ......... 435/320.1 |
| 5,827,703 A | 10/1998 | Debs et al. .................... 514/44 |
| 5,846,782 A | 12/1998 | Wickham et al. .......... 435/69.7 |
| 5,856,152 A | 1/1999 | Wilson et al. ................ 435/457 |
| 5,871,982 A | 2/1999 | Wilson et al. ............ 435/154.1 |
| 5,872,154 A | 2/1999 | Wilson et al. ............ 424/154.1 |
| 5,885,808 A | 3/1999 | Spooner et al. ............. 435/457 |
| 5,895,759 A | 4/1999 | Strauss et al. ............ 435/320.1 |
| 5,910,487 A | 6/1999 | Yew et al. ...................... 514/44 |
| 5,922,576 A | 7/1999 | He et al. |
| 5,980,886 A * | 11/1999 | Kay et al. ................. 424/93.21 |
| 6,265,212 B1 | 7/2001 | Fallaux et al. |
| 6,436,393 B1 | 8/2002 | Bilbao et al. |
| 6,686,198 B1 | 2/2004 | Melton et al. |

FOREIGN PATENT DOCUMENTS

| | | | |
|---|---|---|---|
| WO | WO 96/18419 | * | 6/1996 |
| WO | WO 97/17090 | | 5/1997 |
| WO | WO 98/48024 | | 10/1998 |

OTHER PUBLICATIONS

Oxford Textbook of Clinical Hepatology, vol. 1, (McIntyre et al., eds.) Oxford University Press, 1991, pp. 371-390.*
Foecking et al. Powerful and versatile enhancer-promoter unit for mammalian expression vectors. Gene. 1986;45(1):101-5.*
Lieber et al. A modified urokinase plasminogen activator induces liver regeneration without bleeding. Hum Gene Ther. Aug. 1995;6(8):1029-37.*
Salgado et al. Aguilar-Cordova E, Armendariz-Borunda J. Liver cirrhosis is reverted by urokinase-type plasminogen activator gene therapy. Mol Ther. Dec. 2000;2(6):545-51.*
Dai et al. Advances in gene therapy of liver cirrhosis: a review. World J Gastroenterol. Feb. 2001;7(1):1-8.*
Bramson et al. (1995) Curr. Biol. 6:590-595.*
Weitzman (2005) Frontiers Biosci. 10:1106-1117.*
Armendariz-Borunda, J. et al., "Regulation of TGF Gene Expression in Rat Liver Intoxicated with Carbon Tetrachloride", *FASEB J.*, 1990:4:215-221.
Armendariz-Borunda, J. et al., "Transforming Growth Factor β Gene Expression is Transiently Enhanced at a Critical Stage during Liver Regeneration Following $CCl_4$ Treatment"; *Laboratory Investigation*; 69:283-294, 1993.
Arthur, M. J. P., "Collagenases and Liver Fibrosis", *J. Hepatology*, 1995:22:43-48.
Bradford, M. M., "A Rapid and Sensitive Method for the Quantificaiton of Microgram Quantities of Protein Utilizing the Principle of Protein-Dye Binding", *Anal. Biochem.*, 1976:72:248-54.

(Continued)

*Primary Examiner*—Maria Leavitt
(74) *Attorney, Agent, or Firm*—Morgan, Lewis & Bockius LLP

(57) ABSTRACT

The present invention encompasses a modified human urokinase plasminogen activator ("huPA") gene, which was inserted in the adenoviral vector (pAd-.DELTA.huPA), which is not secreted and does not provoke hypercoagulation or spontaneous internal bleeding. It has been discovered that huPa induced a dramatic fibrosis reduction (85%) on day 10 of vector administration, compared to control cirrhotic rats and 55% hepatocyte proliferation increase. Liver function tests (ALT, AST, alkaline phosphatase and bilirubin) dropped to nearly normal levels and hepatocyte proliferation was observed. The invention also encompasses gene therapy with modified huPA to treat disorders in patients. In a particular embodiment, the invention encompasses a treatment for patients with liver cirrhosis.

2 Claims, 8 Drawing Sheets

OTHER PUBLICATIONS

Brann, T. et al., Adenoviral Vector-Mediated Expression of Physiologic Levels of Human Factor VIII Nonhuman Primates, *Hum. Gene Ther.*, 1999:10:2999-3011.

Corcoran, M. L. et al., "MMP-2: Expression, Activation and Inhibition", *Enzyme Protein*, 1996:49(1-3):7-19.

Delgado-Rizo, V. et al., "Treatment with Anti-Transforming Grown Factor. Antibodies Influences an Altered Pattern of Cytokines Gene Expression in Injured Rat Liver", *Biochem. Biophys.*, Acta, 1998:1442:20-27.

Douglas, J. T. et al., "Adenoviruses as Vectors for Gene Therapy", *Science and Medicine*, Mar./Apr. 1997, pp. 44-53.

Gao, C. et al., Intramuscular of an Hepatic Transduction with a Retroviral Vector in Mice, *Human Gene Ther.*, 1999:10:911-922.

Garcia-Banuelos, J. et al., "Adenovirus-Mediated Gene Delivery to Cirrhotic Rat Livers: Potential Tool for Gene Therapy", *Gene Ther. and Mol. Biol.*, Accepted 2000.

Graham, F. L. et al., "A New Technique for the Assay of Infectivity of Human Adenovirus 5-DNA", *Virology*, vol. 52, pp. 456-467, 1973 53665-5012.

Hattori, N. et al., "Upregulation of Fibrinolysis by Adenovirus-Mediated Transfer of Urokinase-Type Plasminogen Activator Genes to Lung Cells in Vitro and In Vivo", *Human Gene Ther.*, 1999:10:215-222.

Kim, T. H. et al., "Extracellular Matrix Remodeling at the Early Stages of Liver Regeneration in the Rat", *Hepatology*, 1997:26:896-904.

Liu, M. L. et al., "Collagenase Pretreatment and the Mitogenic Effects of Hepatocyte Growth Factor and Transforming Growth Factor-Alpha in Adult Rat Liver", *Hepatology*, 1994:19:1521-152.

Liu, M. L. et al., "Uptake and Distribution of Hepatocyte Growth Factor in Normal and Regenerating Adult Rat Liver", *Am. J. Pathol.*, 1994:144:129-140.

Locaputo, S. et al., "Regulatin of Gene Expression During Liver Regeneration of Urokinase Transgenic Mice", *Hepatology*, 1999:29:1106-1113.

Mariani, S. et al., "Knocking Out Alcohol Damage", *Nature Med.*, 1999:5(11):1243.

Mars, W. M. et al., Activation of Hepatocyte Growth Factor by the Plasminogen Activators uPA and tPA, *Am. J. Pathol.*, 1993:143:949-958.

Michalopoulos, G. K. et al., "HGF in Liver Regeneration and Tumor Promotion", *Prog. Clin. Biol. Res.*, 1995:391:179-185.

Michalopoulos, G. K. et al., "Liver Regeneration", Science, 1997:276:60-66 Nogase, H. et al., "Substrate Specific and Activation Mechanisms of Matrix Metalloproteinases", *Biochem. Soc. Trans.*, 1991(3)715-8.

Nyberg-Hoffman, C. et al., "Sensitivity and Reproducibility in Adenoviral Infectious Titer Determination", *Nature Med.*, 1997:3(7):808-11.

Olaso, E. et al., "Molecular Regulation of Hepatic Fibrogenesis", *J. Hepatology*, 1998:29:836-847.

Roselli, H. T. et al., iver Regeneration is Transiently Impaired in Urokinase-Deficient Mice, *Am. J. Phisiol.*, 1998:275:G1472-G1479.

Schirmacher, F. et al., "The Role of Ito Cells in the Biosynthesis of HGF-SF in the Liver", *EXS* 1993:65:285-299.

Steler-Stevenson, W. G., "Dynamics of Matrix Turnover During Pathologic Remodeling of the Extracellular Matrix", *Am. J. Pathol.*, 1996:148:1345-1350.

Verheijen, J. M. et al., "Modified Proenzymes as Artificial Substrates for Proteolytic Enzymes: Colorimetric Assay of Bacterial Collagenase and Matrix Metalloproteinase Activity Using Modified Pro-Urokinase", *Biochem. J.*, 1997:323 (Pt3):603-609.

Wolf, H. K. et al., "Localization of Hepatocyte Growth Facotr in Human and Rat Tissues: An Immunohistochemical Study", *Hepatology*, 1991:14488-494.

Zern, M. A. et al., "Hepatic Drug Delivery and Gene Therapy", *Hepatology*, 1997, vol. 25, No. 2, 484-491 61537-0032.

Anthony, P. P., et al.: "The Morphology of Cirrhosis: Definition, Nomenclature and Classification", Bulletin of the World Health Organization; 55: 521-540, 1977.

Armendariz-Borunda, J. et al.: "A Simple Quantitative Method for Collagen Typing in Tissue Samples: Its Application to Human Liver with Schistosomiasis"; Collagen Rel. Res., 4: 35-47, 1984.

Armendariz-Borunda, J. et al.: "Activation of Ito Cells Involves Regulation of AP-1 Collagen Gene Expression"; Biochemical Journal, 304: 817-824, 1994.

Armendariz-Borunda, J. et al.: "Transcriptional Mechanisms of Type I Collagen Gene Expression are Differentially Regulated by Interleukin-1 $\beta$, Tumor Necrosis Factor $\alpha$, and Transforming Growth Factor $\beta$ in Ito Cells", J. Biol. Chem., 267: 14316-14321, 1992.

Baker et al., "Development of recombinant adenoviruses that drive high level expression of the human metalloproteinase-9 and tissue inhibitor of metalloproteinase-1 and -2 genes: characterization of their infection into rabbit smooth muscle cells and human MCF-7 adenocarcinoma cells", Matrix Biology, 15: 383-395, 1996.

Brinckerhoff et al., "Molecular cloning of human synovial cell collagenase and selection of a single gene from genomic DNA", Journal of Clinical Investigation, 79: 542-546, 1987.

Carmeliet et al.: "Adenovirus-mediated transfer of tissue-type plasminogen activator augments thrombolysis in tissue-type plasminogen activator-deficient and plasminogen activator inhibitor-1-overexpressing mice", Blood, 4: 1527-1534, 1997.

Chen, C. et al.: "Calcium Phosphate-Mediated Gene Transfer: A Highly Efficient Transfection System for Stably Transforming Cells with Plasmidic DNA", Biotechniques, 6: 632-638, 1998.

Davis, C. G., "The many faces of epidermal growth factor repeats", The New Biologist, 2(5): 410-419, 1990.

Deonarain, M., "Ligand-targeted receptor-mediated vectors for gene delivery", Expert Opin. Ther. Pat., 8: 53-69, 1998.

Devarajan et al., "Structure and expression of neutrophil gelatinase cDNA. Identity with type IV collagenase from HT1080 cells", The Journal of Biological Chemistry, 267(35): 25228-25232, 1992.

Douglas, J. T. et al.: "Adenoviruses as Vectors for Gene Therapy", Science and Medicine, Mar./Apr., p. 44-53, 1997.

Dumaswala, R. et al.: "Adaptive Response of the Enterohepatic Circulation of Bile Acids to Extrahepatic Cholestiasis", Hepatology, 23(3): 623-629, 1996.

Eck et al., Goodman & Gilman's The Pharmacological Basis of Therapeutics, McGraw-Hill NY p. 77-101, 1996.

Fernandez et al., "Modulation of matrix metalloproteinase activity in human saphenous vein grafts using adenovirus-mediated gene transfer", Surgery, 24: 129-136, 1998.

Freije et al., "Molecular cloning and expression of collagenase-3, a novel human matrix metalloproteinase produced by breast carcinomas", Journal of Biological Chemistry, 269(24): 16766-16773, 1994.

Friedman, S. L. et al.: "The Cellular Basis of Hepatic Fibrosis: Mechanisms and Treatment Strategies", The New England Journal of Medicine, 1993, vol. 328(25), pp. 1828-1835.

Gorecki, "Prospects and problems of gene therapy: an update", Expert Opin. Emerging Drugs, 6(2): 187-198, 2001.

Gros et al., "Regulated production of mature insulin by non-beta-cells", Human Gene Therapy, 8(18): 2249-2259, 1997.

Hasty et al., "Human neutrophil collagenase. A distinct gene product with homology to other matrix metalloproteinases", The Journal of Biological Chemistry, 265(20): 11421-11424, 1990.

He, T-C et al.: "A Simplified System for Generating Recombinant Adenoviruses", Proc. Natl. Acad. Sci. USA, vol. 95: 2509-2514, 1998.

Jaffe et al., "Selective inhibition of collagen gene expression in fibroblasts by an interferon-gamma transgene", Experimental Lung Research, 25(3): 199-215, 1999.

Kaye et al., "A single amino acid substitution results in a retinoblastoma protein defective in phosphorylation and oncoprotein binding", Proc. Natl. Acad. Sci. USA, 87: 6922-6926, 1990.

Lee, S. et al.: "Hemodynamic Characterization of Chronic Bile Duct-Ligated Rats: Effect of Pentobarbital Sodium", AM Journal Fisiol., 1986; 251:176-180.

Li, et al., "Regulatable production of insulin from primary-cultured hepatocytes: insulin", Gene Therapy, 5: 888-895, 1998.

Ludin et al., "Application of novel vectors for GFP-tagging of proteins to study microtubule-associated proteins", Gene, 173: 107-111, 1996.

Marie-Jeanne T.F.D. Vrancken Peeters, et al.: "Methods for Multiple Portal Vein Infusion in Mice: Quantitation of Adenovirus-Mediated Hepatic Gene Transfer", Bio Techniques, 1996; 20:278-285.

Martinez-Fong, D. et al.: "Nonenzymatic Glycosylation of Poly-L-lysine: A New Tool for Targeted Gene Delivery", Hepatology, vol. 20(6): 1602-1608.

Mion, F. et al.: "Carbon Tetrachloride Induced Cirrhosis in Rats: Influence of the Acute Effects of the Toxin on Glucose Metabolism", Hepatology, 1996, vol. 23(2):582-587.

Nakano, S. et al.: "Alteration in Bile Ducts and Peribiliary Microcirculation in Rats After Common Bile Duct Ligation", Hepatology, 21(5): 1380-1386, 1995.

Poo, J. L., et al.: "Cronologia de Hipertension Portal, Disminucion de Excrecion de sodio y activacion del sistema renina-angiotensina en cirrosis biliar experimental", Rev., Invest Clin., 49: 15-23, 1997.

Rojas-Martinez, A. et al.: "Distribution, Persistency, Toxicity and Lack of Replication of an EI A-Deficient Adenoviral Vector after Intracardiac Delivery in the Cotton Rat", Cancer Gene Ther., 5: 365-370, 1998.

Rudinger, Peptide Hormones, Edited by Parsons, University Park Press, Baltimore, p. 1-7, 1976.

Shimohama, S. et al.: "Grafting Genetically Modified Cells into the Rat Brain: Characteristics of $E.\ coli$ β-Galactosidase as a Reporter Gene", Molecular Brain Res., 5: 271-278; 1989.

Skolnick et al., "From genes to protein structure and function: novel applications of computational approaches in the genomic era", Trends in Biotech, 18: 34-39, 2000.

Thomas et al., "Progress and problems with the use of viral vectors for gene therapy", Nature Reviews/Genetics, 4: 346-358, 2003.

Varga et al., "Systemic sclerosis: a prototypic multisystem fibrotic disorder", The Journal of Clinical Investigation, 117(3): 557-567, 2007.

Verma et al., "Gene therapy—promises, problems and prospects", Nature, 389: 239-242, 1997.

Weiss, D. J. et al.: "In Situ Histochemical Detection of β-Galactosidase Activity in Lung: Assessment of X-Gal Reagent in Distinguished *lacZ* Gene Expression and Endogenous β-Galactosidase Activity", Human Gene Therapy, 8: 1545-1554, 1997.

Zhu, G. et al.: "Adenovirus-Mediated β-Galactosidase Gene Delivery to the Liver Leads to Protein Deposition in Kidney Glomeruli", Kidney International, 52: 992-999, 1997.

\* cited by examiner

SEQUENCE LISTING

<160> NUMBER OF SEQ ID NOS: 9

<210> SEQ ID NO 1
<211> LENGTH: 19
<212> TYPE: DNA
<213> ORGANISM: Artificial Sequence
<220> FEATURE:
<223> OTHER INFORMATION: Primer(sense) for amplify HGF gene

<400> SEQUENCE: 1
atgctcattg gaccctggt                                              19

<210> SEQ ID NO 2
<211> LENGTH: 18
<212> TYPE: DNA
<213> ORGANISM: Artificial Sequence
<220> FEATURE:
<223> OTHER INFORMATION: Primer(antisense) for amplify HGF gene

```
<400> SEQUENCE: 2
gcctggcaag cttcatta                                                    18

<210> SEQ ID NO 3
<211> LENGTH: 23
<212> TYPE: DNA
<213> ORGANISM: Artificial Sequence
<220> FEATURE:
<223> OTHER INFORMATION: Artificial Sequence Primer(sense) for amplify
      c-met gene

<400> SEQUENCE: 3
cagtgatgat ctcaatgggc aat                                              23

<210> SEQ ID NO 4
<211> LENGTH: 22
<212> TYPE: DNA
<213> ORGANISM: Artificial Sequence
<220> FEATURE:
<223> OTHER INFORMATION: Artificial Sequence Primer(antisense) for
      amplify c-met gene

<400> SEQUENCE: 4
aatgccctct tcctatgact tc                                               22

<210> SEQ ID NO 5
<211> LENGTH: 21
<212> TYPE: DNA
<213> ORGANISM: Artificial Sequence
<220> FEATURE:
<223> OTHER INFORMATION: Primer(sense) for amplify collagen I gene

<400> SEQUENCE: 5
caagaatggc gaccgtggtg a                                                21

<210> SEQ ID NO 6
<211> LENGTH: 21
<212> TYPE: DNA
<213> ORGANISM: Artificial Sequence
<220> FEATURE:
<223> OTHER INFORMATION: Primer(antisense) for amplify collagen I gene

<400> SEQUENCE: 6
ggtgtgactc gtgcagccat c                                                21

<210> SEQ ID NO 7
<211> LENGTH: 20
<212> TYPE: DNA
<213> ORGANISM: Artificial Sequence
<220> FEATURE:
<223> OTHER INFORMATION: Primer(sense) for amplify collagen III gene

<400> SEQUENCE: 7
agatggatca agtggacatc                                                  20

<210> SEQ ID NO 8
<211> LENGTH: 20
<212> TYPE: DNA
<213> ORGANISM: Artificial Sequence
<220> FEATURE:
<223> OTHER INFORMATION: Primer(antisense) for amplify collagen III gene

<400> SEQUENCE: 8
catgtttctc cggtttccat                                                  20
```

```
<210> SEQ ID NO 9
<211> LENGTH: 7
<212> TYPE: PRT
<213> ORGANISM: Artificial Sequence
<220> FEATURE:
<223> OTHER INFORMATION: Arginin residues in RR sequence

<400> SEQUENCE: 9

Met His Arg Arg Arg Ser Arg
1               5
```

RECOMBINANT VIRAL AND NON-VIRAL VECTORS CONTAINING THE HUMAN UROKINASE PLASMINOGEN ACTIVATOR GENE AND ITS UTILIZATION IN THE TREATMENT OF VARIOUS TYPES OF HEPATIC, RENAL, PULMONARY, PANCREATIC AND CARDIAC FIBROSIS AND HYPERTROPHIC SCARS

TECHNICAL FIELD OF THE INVENTION

The present invention relates to the creation of recombinant viral, non viral, plasmidic and synthetic vectors having the human gene of urokinase derived plasminogen activator cloned, hereinafter huPA cDNA (complementary DNA). It is also related to the utilization of the TGF-beta type II truncated receptor gene. The viral vectors used can be, without limitation, first, second, third and/or fourth generation adenoviral vectors, "gutless" adenoviral vectors, retroviral vectors, adeno-associated vectors. Non-viral vectors can be constituted of phospholipid components, liposomes of various structures and combined through different ligands for specific receptors. Synthetic vectors can consist of the construction and coupling of huPA cDNA and TGF-beta type II truncated receptor with plasmids from different origins and regulatable promoters. huPA cDNA encodes for therapeutic proteins useful in the treatment of hepatic cirrhosis and generalized fibrosis, such as renal fibrosis, pulmonary fibrosis, pancreatic fibrosis, heart fibrosis, hypertrophic scars and keloids (skin scars) and/or in other target organs susceptible of suffering from it. It also relates to a mechanism of tissue-specific recognition of the affected cells in vivo by means of delivery of therapeutic huPA gene to organs chronically affected by fibrosis.

Moreover, the invention provides an effective way for the treatment of fibrosis through the use of recombinant vectors which are claimed here, as well as the process involve in the preparation of these vectors, the pharmaceutical composition containing them, the treatment methods and their therapeutic uses in fibrosis treatment, which has great commercial potential in the pharmaceutical industry and also presents an important alternative as experimental gene therapy for the treatment of chronic-degenerative diseases characterized by fibrosis, with important therapeutic application in the field of modern medicine.

INTRODUCTION

Epidemiology and Physiopathology of Hepatic Cirrhosis

Hepatic cirrhosis represents a world health problem because it is an important mortality cause. It is a terminal illness usually caused by chronic alcohol ingestion and hepatitis C infection and there is no definite available treatment when it affects adults. About 14 million people are affected by alcoholism in the USA and the figure is similar in Mexico (Mariani, S., Birmingham, K. and Novak, K. Knocking out Alcohol Damage. Nature Med. 1999:5(11):1243). Hepatic cirrhosis is considered a severe health problem in Mexico, since it is the fourth cause of death in working-age people and there is no 100% effective treatment. Moreover, hepatic cirrhosis is also a cause of death in children due to the consequences of biliary obstruction. However, in this case, the incidence is much lower and the surgical approach through Kasai shunt mitigates the illness during a few months. However, 50% of the children who undergo said surgery die during the following months and the rest of them who partially respond to the shunt effects are channeled to a possible liver transplantation. Currently, there are gene therapy protocols for other chronic-degenerative illnesses, but up to now no protocol has been reported in which a gene therapy is used to cure cirrhosis. Thus, in the instant invention, this gene therapy protocol has been developed at preclinical level. Its further use with human beings will depend on the successful and safe sending of genes coding for therapeutic proteins in livers with extensive fibrosis, using as the main sending strategy, viral, non-viral, plasmidic and synthetic vectors. For this purpose, a preclinic study was previously conducted to determine the safety, transduction efficacy, toxicity and bio-distribution of an adenoviral vector bearing as reporter gene the gene lacZ in cirrhotic Wistar rats (Mexican Patent Application # 998515, pending). Once the potential use of adenoviral vectors has been shown for sending exogenous genes to damaged livers without notably worsening its function, the effect of "therapeutic genes" on cirrhotic livers was evaluated.

Hepatic cirrhosis is characterized by a fibrosis increase where there is an accumulation of extracellular matrix proteins (especially I, IV and III type collagen) synthesized by hepatic stellate cells (Arthur, M. J. P. Collagenases and liver fibrosis, J. Hepatology 1995:22:43-48; Kim, T. H. Mars, W. M., Stolz, D. B., Petersen, B. E., and Michalopoulos, G. K. Extracellular matrix remodeling at the early stages of liver regeneration in the rat. Hepatology 1997:26:896-904; and Olaso, E. and Friedman, S. L. Molecular regulation of hepatic fibrogenesis. J. Hepatology 1998:29:836-847) throughout liver parenchyma, mainly around the central and portal veins, forming a barrier blocking the free exchange of nutrients between the sinusoid and the hepatocytes leading to function deterioration (FIG. 1A) (Arthur, M. J. P. Collagenases and liver fibrosis, J. Hepatology 1995:22:43-48; and Kim, T. H. Mars, W. M., Stolz, D. B., Petersen, B. E., and Michalopoulos, G. K. Extracellular matrix remodeling at the early stages of liver regeneration in the rat. Hepatology 1997:26:896-904). Thus, the inventors of the instant invention suggest as a theory that recombinant viral and non viral vectors could be used in gene therapy to revert exacerbated fibrosis, the cardinal characteristic of cirrhotic livers, and, in turn, with the induction of genes promoting liver cell proliferation, enhance the rapid reestablishment of functional liver mass. For this purpose, in said vectors, the modified DNA of human urokinase plasminogen activator (huPA), that activates a cascade (lower part of FIG. 1B), wherein, on the one hand it activates latent liver collagenases or matrix metalloproteases (MMPs) to promote the degradation in situ of excess extracellular matrix (ECM) in the perisinusoidal space or space of Disse. The deposited excess extracellular matrix blocks nutrient exchanges between hepatocytes and circulating blood and thus the liver function is affected. Concomitantly, huPA restores the functional liver mass inducing the replication of the remaining hepatocytes and thus repopulate liver parenchyma (FIG. 1B). The reason to use said recombinant vectors is because of the additional advantage that because they do not secrete significant amount of huPA, they do not cause hypocoagulation or spontaneous bleeding which is the main disadvantage in cirrhotic animals. In this way, inducing two different cascades of beneficial events, the modified huPA cADN therapy can be very useful for the treatment of liver cirrhosis. It is important to observe that up to date no therapeutic agent reverting and/or preventing with 100% effectiveness the progressive accumulation of liver collagen has been described.

Such physiopathological alterations occurring in hepatic cirrhosis are constant and common for the other organs that also undergo fibrosis, such as, lung, heart, kidney, pancreas and skin, among others, which should be not considered as limitations of the scope of protection of this invention. Therefore, the methodology presented here for the treatment of hepatic cirrhosis could be applied also to those organs that are susceptible to, or are affected by fibrosis.

Viral and Non-viral Vectors in Hepatic Gene Therapy

The viral vectors used in this invention to implement this technology can be, without limitation, first, second, third and/or fourth generation adenoviral vectors, "gutless" adenoviral vectors, retroviral vectors and adeno-associated vectors. The non-viral vectors can be constituted by plasmids, phospholipids, liposomes (cationic and anionic) of different structures and combined with different ligands for specific receptors. The synthetic vectors consist of the construction and coupling huPA cDNA and TGF-beta Type II truncated receptor cDNA with plasmids from different origins and with regulatable and/or inducible promoters. In many protocols, retroviral vectors have been used to introduce genes in hepatocytes (Douglas J. T., and Curiel D. T., Adenoviruses as Vectors for Gene Therapy. Science and Medicine March/April 1997 44-53). However, precautions have to be taken since these vectors can generate potential replication-competent viruses. Among the advantages of these vectors is their ability to integrate their genome in a stable way in the chromosomes of the guest cell, which confers the possibility of expression, in an indefinite way, of the therapeutic transgene cloned in the retrovirus. On the other hand, up to date, no study has reported incidences of mutagenesis by insertion or activation of oncogenes through retrovirus integration if the viruses used are not replication-competent. Nevertheless, the use of retroviral vectors to transduce genes to the liver is limited for the following considerations: 1) these vectors infect only cells which actively divide and 2) very low viral particles titers are obtained in the packing cell lines used to amplify these viruses (Graham F. L., and Van Der Eb A J. A New Technique for the Assay of Infectivity of Human Adenovirus 5 DNA. Virology 1973, 52:456-467). These two limitations have been successfully overcome in other gene therapy protocols through the induction of hepatocytes proliferation in vivo, through the use of hepatic growth factors and through partial hepatectomy, surgical procedure through which the removal of 70% of liver mass induces division of the remaining hepatic cells in vivo. The use of lentiviral vectors has permitted to overcome partially said limitations, because they are able to transduce cells which are not actually dividing.

BACKGROUND OF THE INVENTION

Hepatic cirrhosis is a chronic illness of the liver, where diffuse cell necrosis and a limited regeneration of parenchymal hepatic cells result in diffuse percentage increase of connective tissue, causing the distortion of lobular hepatic architecture and inducing hemodynamic alterations. Therefore, some strategies for the treatment of hepatic cirrhosis could include the prevention and/or reversion of the fibrogenesis, stimulation of hepatic mitosis and re-arrangement of the architecture of hepatic tissue. The documents of the state of the art related to the present invention are mentioned hereinafter only as references.

U.S. Pat. No. 5,240,846 relates to the use of gene therapy called "CFTR", which induces a stable correction of the regulation of the chlorine channel. This defect is present in epithelial cells. In said invention, adenoviral recombinant vectors are used as well as plasmidic vectors. However, it does not have any association with the therapeutics genes of the present invention. Likewise, U.S. Pat. No. 5,910,487 describes the use of plasmidic vectors for sending therapeutic molecules, but there is no association with the delivery of wild and/or modified huPA genes or of the TGF-beta (Transforming Growth Factor-beta) Type II truncated receptor genes as presented here. U.S. Pat. No. 5,827,703 refers to the use of adenoviral vector and modified adenoviral vector to send genes, however, none of these vectors contain the genes used in the present invention for the treatment of fibrosis.

U.S. Pat. No. 5,770,442 claims the use of a recombinant adenovirus that contains one gene directing the expression of a protein called "fiber" or a protein called "fiber-chimera", however said patent does not specifically mention, which one is the therapeutic gene. Moreover, a method of gene therapy involving the use of such adenovirus and a vector of transference for the generation of such recombinant adenovirus is presented. However, nothing is mentioned with regard to the use of therapeutic genes cloned arid inserted in recombinant adenoviral vectors used in this invention in fibrotic livers, or to other target organs such as kidney, lung, and hypertrophic scars and others. These therapeutic genes are the gene that codes for the wild and/or modified huPA activator and the TGF-beta (Transforming Growth Factor-beta) type II truncated receptor, claimed in the instant invention. Other members of the family of genes represented are also included.

U.S. Pat. No. 5,166,320 refers to the use of a targeted delivery system to introduce exogenous genes in mammalian hepatic cells. But there is no association with putative genes directly sent to fibrotic livers, kidneys, lungs or other fibrotic organs.

U.S. Pat. No. 5,872,154 describes a method to reduce the immune response induced by an adenoviral recombinant vector through co-administration of recombinant adenoviral vector and a selected immune modulator, which functions by inhibiting the formation of neutralizing antibodies and/or reducing the death of the virally infected cells. U.S. Pat. No. 5,871,982 is directed to a hybrid vector, in which a portion of an adenovirus is included, together with a portion of an adeno-associated viral vector that contains a selected transgene. A hybrid virus consisting of the union of a conjugate with a polycation to a gene mesh of the adeno-associated viral vector to form a simple particle is also described. This is contrary to the present invention in which no hybrid viruses are employed, only adenoviral vectors. Besides, in the above-mentioned patent the gene, transgene or therapeutic gene used is not stated. U.S. Pat. No. 5,856,152 is directed to the creation of a hybrid vector that contains the portion of an adenoviral vector in combination with an adeno-associated virus and a selected gene, through which large quantities of recombinant vectors are produced, but they are not carrying cloned therapeutic genes as described in this invention, in which specific therapeutic genes for the treatment of liver, kidney, pancreas, heart fibrosis as well as keloids and hypertrophic scars are used. U.S. Pat. No. 5,547,932 claims a compound of nucleic acid complexes for transfecting eucaryotic cells. These complexes are formed by nucleic acids and another substance with affinity for nucleic acids and optionally an internalizing factor, such as a virus or a component of the virus that can be conjugated. It also uses components of specific adenoviral vectors or specific viruses such as Ad2 or Ad5, but does not mention the genes that are internalized in the cell cytoplasm and eventually in the nucleus of these eucaryotic cells. Similarly, U.S. Pat. No. 5,521,291 relates to conjugated adenovirus bound through an antibody to a substance with affinity for nucleic acids. In this way recombinant genes are transported to the interior of eucaryotic cells. These conjugated complexes and nucleic acids are internalized in the cell, but the genes that can be sent are not specifically mentioned. In said patent, contrary to what is described in the instant invention, the use of such adenovirus to treat liver fibrosis or cirrhosis or any another type of fibrosis is not mentioned.

U.S. Pat. No. 5,585,362 relates to an improved adenoviral vector and methods to obtain and use such vectors. Although the use of adenoviral vectors is not mentioned in said patent, the adenoviral vectors described in the present invention were used as vectors for sending therapeutic genes.

U.S. Pat. No. 5,756,086 claims an adenovirus, which is represented by a protein called "fiber". The adenovirus also includes a ligand, that is specific for a receptor located on a specific cell type. This adenovirus can have at least a portion of this protein called "fiber" and it can be removed and replaced with a ligand, which is specific for a receptor on specific cells, such as hepatocytes. These adenoviruses can include a gene that codes for a therapeutic agent. Based on the previous statement, the outstanding technical difference of the instant invention, compared to the state of the art, is the specificity of the therapeutic agent as wild and/or modified huPA and the TGF-beta type II truncated receptor for the treatment of various fibrosis.

U.S. Pat. No. 5,895,759 claims a tissue-specific vector (liver) for gene therapy that can be used to send genes to a damaged liver. These vectors are chemically or enzyme coupled to a promoter and can also be coupled to an antibody packaged in a polypeptidic envelope. Besides, the vector or the virus to be assayed is the hepatitis B virus. Thus the sending of genes to damaged livers described in this patent makes use of a system completely different from the one of this invention, and there is no relation with the process of fibrosis or cirrhosis to be treated. U.S. Pat. No. 5, 559,099 describes an adenoviral recombinant vector that contains a chimeric protein from the adenovirus called pentona, which includes a non-pentona sequence and a therapeutic gene to develop a gene therapy method involving the use of such adenovirus, transference adenoviral vectors for the recombination of such adenoviral vectors containing a therapeutic gene. Moreover, U.S. Pat. No. 5,885,808 claims also the use of adenovirus with bonding molecules of adenovirus to different cells, the molecules of which have been modified, as in U.S. Pat. Nos. 5,846,782 and 5,712,136, in which adenoviral vectors are employed, which have been modified to contain different peptidic domains.

Finally, U.S. Pat. No. 5,670,488 relates to vectors for gene therapy, which are especially useful for cystic fibrosis and also mentions the development of methods for the use of these vectors. The possible relation of the instant invention to the mentioned state of the art refers to the use of adenoviral vectors, that can be modified, as well as the use of inducible promoters driving the expression of genes to be inserted in these adenoviral vectors. However, the technical characteristics of the present invention are focused on the specific use of therapeutic genes to treat different types of fibrosis such as liver, kidney, lung, pancreas, heart fibrosis, keloids, as well as hypertrophic scars.

The importance of the present invention, contrary to the state of the art described in the above-mentioned documents, is based on the technical characteristics of the invention itself, as well as on the additional advantages derived from the same, which are described with more details below.

Adenoviral Vectors

In the instant invention the decision has been made to use adenoviral vectors, although it is important to stress that the viral vectors used to implement this technology can be, not restrictively, first, second, third and/or fourth generation adenoviral vectors, "gutless" adenoviral vectors, retroviral vectors, adeno-associated vectors. The non-viral vectors can be constituted by plasmids, phospholipidic components, (cationic and anionic) liposomes of different structures and combined with different ligands for specific receptors. The synthetic vectors are prepared through the construction and coupling of huPA cDNA and the TGF-beta type II truncated receptor with plasmids from different origins and with regulatable and/or inducible promoters.

The adenoviral vectors were initially selected based on several considerations: 1) these vectors can be generated to very high titers of infectious particles per ml.: ($10^9$-$10^{10}$); 2) they infect a great variety of cells, however, when they are administered i.v., most of them are located in the hepatic organ; 3) they transfer efficiently genes to cells that are not dividing, and 4) they are seldom integrated in the guest genome, which avoids the risk of cellular transformation by insertional mutagenesis (Douglas J. T., and Curiel D. T. Adenoviruses as Vectors for Gene Therapy. Science and Medicine, March/April 1997. 44-53 and Zern A M, and Kresina T F. Hepatic Drug delivery and Gene Therapy (Hepatology 1997, Vol. 25, No. 2, 484-491).

Adenovirus are probably the most promising vehicles or vectors for the delivery of genes in the protocols of gene therapy in human beings, since they possess a unique attribute that provides them great stability when they are administered into the blood stream. This specific characteristic permits them to be efficiently used in clinical trials with a comfortable i.v. administration for the patient. (Douglas J. T., and Curiel D. T. Adenoviruses as vectors for Gene Therapy. Science and Medicine, March/April, 1997, 44-53).

Adenoviruses are double stranded DNA viruses. They have an icosahaedric structure, infect a great variety of mammalian cell types, and support the ubiquitous expression of a specific receptor in the cell surface not yet identified. Their union to cells occurs by means of the protein component of the adenovirus capside and the virus enters into the cell by receptor-mediated endocytosis.

More than 40 different human serotypes of adenovirus have been identified, of which type 2 (Ad2) and 5(Ad5) have been more extensively studied and, therefore, more widely used as vectors for gene therapy. A very important characteristic of these two Ad serotypes is that they have never been associated with malignant human processes.

The strategy for the creation of recombinant adenovirus is based on the organization of the adenoviral genome. The expression of the adenoviral genes occurs in two phases, early and late, that are defined by the time of replication of the adenoviral genome. The early genes encode themselves in 4 distinct transcriptional units. E1, E2 and E4 encode for essential regulatory proteins that induce the replication of the adenoviral DNA. The gene E3 is a non-essential gene. The products of the late genes include the main proteins of the capside, which are transcribed from a unique promoter. (Graham F. L., and Van Der Eb A J. A New Technique for the Assay of Infectivity of Human Adenovirus 5 DNA. Virology 1973, 52:456-467).

The recombinant adenoviruses are generated by introduction of the exogenous gene or sequence of DNA of interest in substitution of the adenoviral genome regions required for the replication of the virus. The adenoviral recombinant vectors present deletions in E1 and E3 genome regions. Recombinant adenovirus generation is conducted both through the replacement of E1 or E3 regions or through the insertion of the exogenous gene between the E4 region and the extreme right part of the adenoviral genome. Vectors based on the insertion of the exogenous gene at the extreme right part of the adenoviral genome or by the replacement of the E3 region keep their replication capability. On the contrary, the substitution of early region E1 produces a vector which is faulty with regard to its replication capability, that can spread only in a cell line that supplies in "trans" the absent functions of the replaced adenoviral region, or in presence of a collaborator virus. Among them, the most commonly used as gene transference vectors are the replication-deficient adenovirus (Douglas J. T., and Curiel D. T. Adenoviruses as Vectors for Gene Therapy. Science and Medicine, March/April, 1997, 44-53).

The creation of adenoviral vectors, as well as their application for the treatment of fibrosis, are shown in the examples described hereinafter.

OBJECTS OF THE INVENTION

Hereinafter, the objects and advantages derived from this invention are presented.

An object of the present invention is to provide a procedure to prepare recombinant adenoviral vectors AdΔhuPA, by means of the cloning of huPA modified cDNA in appropriate adenoviral vectors; besides, huPa cloning in "gutless", adeno-associated vectors and the formation of liposome and phospholipid component complexes.

Another object of the invention is to provide adenoviral recombinant vectors (all the previously mentioned in the instant invention), with an exogenous gene or DNA sequence of interest that encodes for therapeutic proteins useful in the treatment of the generalized fibrosis in target organs susceptible to suffer from it. Such gene is, but not restrictively, a wild and/or modified huPA gene or the TGF-beta (Transforming Growth Factor-beta) type II truncated receptor gene.

Also, in the present invention, pharmaceutical compositions (or other compositions) are provided which contain the recombinant viral, non-viral, plasmidic vectors in quantities therapeutically effective of viral particles for the treatment of generalized fibrosis; as well as therapeutic treatment methods, their uses and therapeutic applications in the treatment of fibrosis.

An advantage of greater importance in the treatment of the generalized fibrosis, particularly of hepatic cirrhosis, is that the delivery of therapeutic gene(s) is carried out through tissue-specific recognition by the route of administration employed and by the natural tropism to the cirrhotic liver of the recombinant vectors used.

Another advantage of the therapeutic uses of the invention, which is directed initially to the treatment of hepatic cirrhosis, is the treatment of generalized fibrosis in other target organs susceptible to suffer from it, including, not restrictively, the treatment of liver, lung, heart, skin, kidney, pancreas fibrosis, among others, in mammalian animals, including human beings.

Another object is the design of a technology to deliver genes efficiently first to livers of cirrhotic animals affected by cirrhosis induced by carbon tetrachloride ($CCl_4$) and common biliary obstruction. This type of cirrhosis experimental models is very similar to the two types of liver cirrhosis that usually affect human beings in Mexico and in the rest of the world (alcoholic cirrhosis, chronic infection caused by hepatitis C virus, and secondary biliary cirrhosis).

Another advantage resulting from the fibrosis treatment is that the recombinant adenovirus used (and none of the other proposed adenoviral vectors) does not induce lethal toxicity in the animals injected with the vectors.

Another object of the invention allows us to conclude that liver fibrosis is totally resolved, and that the proliferation of liver cells is dramatically stimulated, obtaining thus the reestablishment of liver function in cirrhotic animals.

Another advantage of the design of this technology is the fact that it is possible to detect the expression of human uPA therapeutic gene delivered to cirrhotic animals through the expression of the corresponding human protein through ELISA essays and through immunohistochemistry. We can thus discriminate between the endogenous rat protein and the therapeutically induced protein production. Thus, this allows us to check the transduction in vivo of the different organs of the rat to see if the vector administration was adequate and if the expression remains only in the target organ.

Finally, all this evidence allows us to suggest that our system comprises an efficient and adequate vehicle to deliver therapeutic genes such as wild and/or modified huPA and the TGF-beta (Transforming Growth Factor-beta) type II truncated receptor that degrade the excess collagen and/or prevent its deposition; and that produce protein stimulating liver regeneration, to cirrhotic rat livers in order to restore normal functions of the liver or other organs affected by the same pathology.

Thus, in the present invention a process of preparation is given for recombinant adenoviral vectors and other viral and non-viral above-mentioned vectors, pharmaceutical compounds, therapeutic treatment methods, uses and therapeutic applications for the treatment of fibrosis, especially for the treatment of hepatic cirrhosis.

BRIEF DESCRIPTION OF THE DRAWINGS

Other particularities and advantages of this invention will be evident from the following detailed description of the preferred objects and embodiments, from the enclosed claims and from the drawings or figures attached, in which:

DETAILED DESCRIPTION OF THE INVENTION

There are many reports showing that through systemic administration of recombinant adenoviral vectors (AdR) into healthy experiment animals, a specific homing and highly preferential tropism of these vectors into the liver is observed. The inventors of the instant invention have shown that the cirrhotic liver is also a favorite target of adenoviral vectors, even though the organ lobular architecture is altered because of the fibrosis established in the entire liver parenchyma, mainly around the central and portal veins.

Therefore, in the instant invention the hypothesis has been established according to which, using a modified cDNA of human urokinase derivate plasmid gene activator (huPA), it could be possible to promote, in damaged livers, the in situ degradation of excess collagen components of the extracellular matrix through latent MMPs activation, and to reestablish the free exchange of macromolecules between the sinusoid and the hepatocytes, as well as the functionality of the hepatocytes affected upon inducing them to proliferate and in this way, repopulate the liver parenchyma and obtain the regeneration and cure of the damaged liver.

Figure 1:
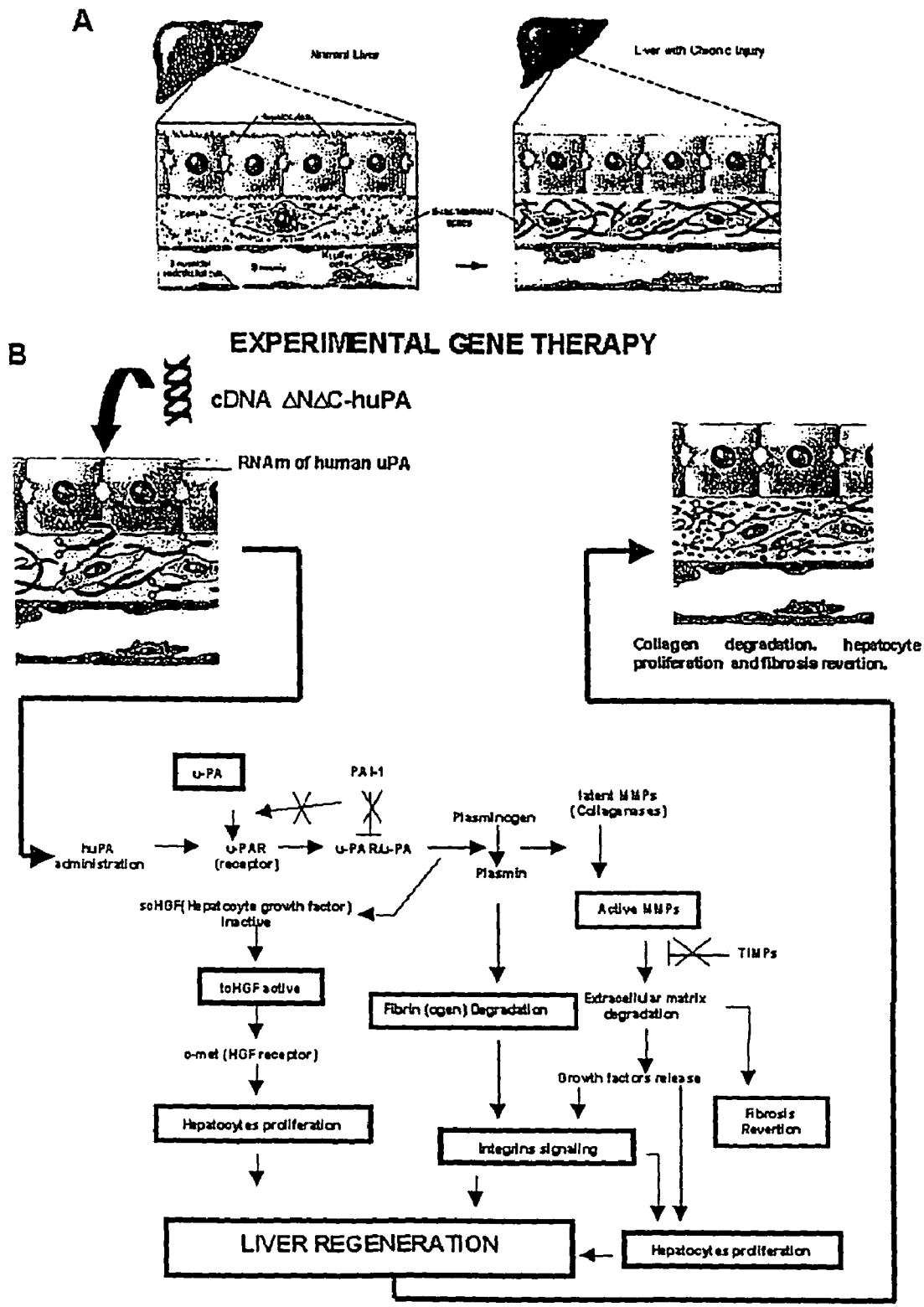
FIG. 1 shows the cellular physiopathology of hepatic cirrhosis (A); and the concept evidence regarding how the gene therapy works to revert the fibrosis process, as well as the cascade of events induced by huPA cDNA leading to fibrosis reversion and liver cell regeneration (B)
Figure 4:
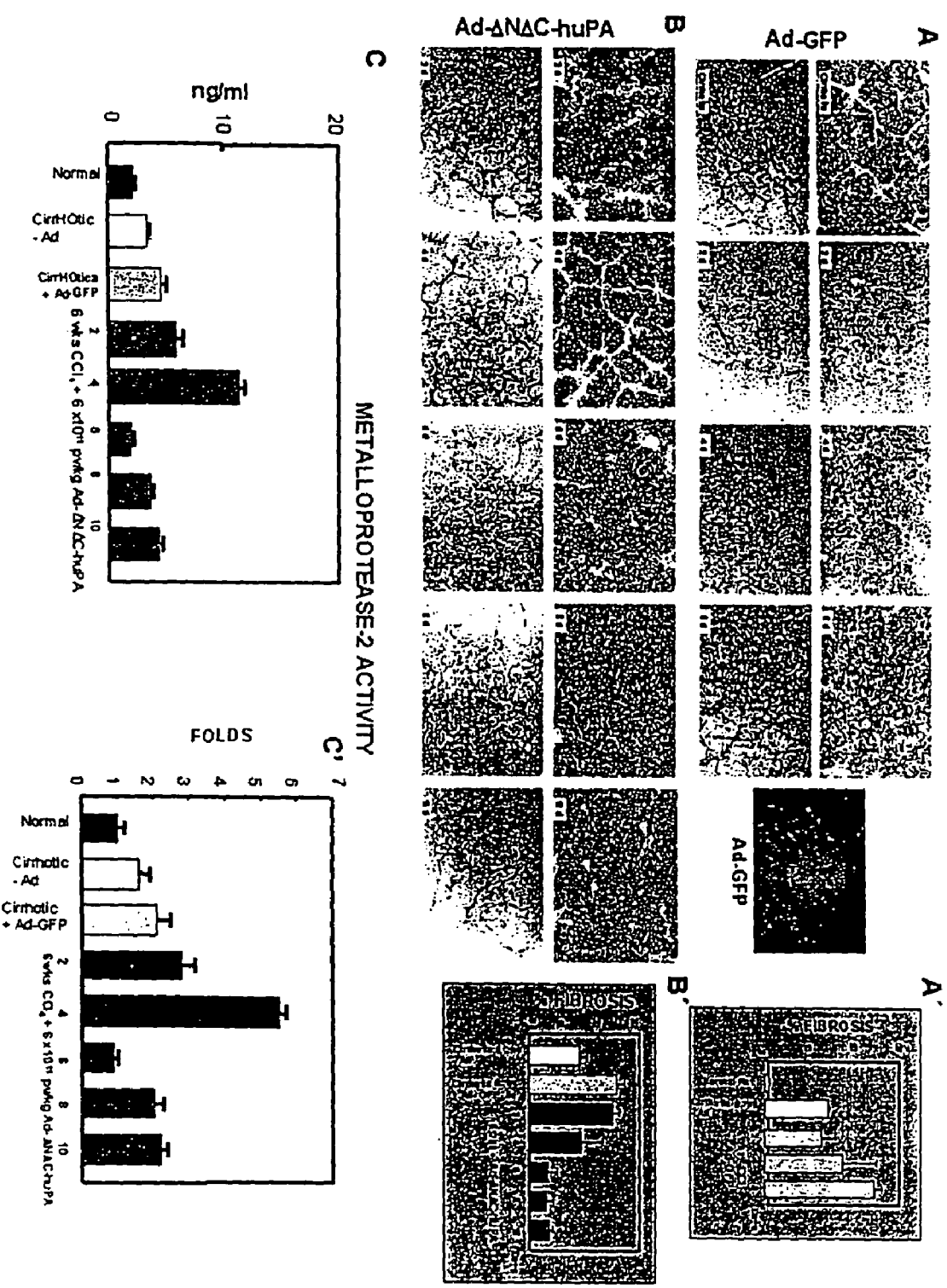
FIG. 4 shows liver histological cuts from rats treated with $CCl_4$ during 6 weeks obtained on different days after the injection of Ad-GFP (A), irrelevant vector, and Ad-ΔNΔC-huPA (B), therapeutic vector, the quantitative determination through morphometrical analysis of fibrosis grade, in each case, and the concomitant induction of metalloprotease 2 (MMP-2) activity is also shown (C and C'). The expression of the protein product of fluorescent green gene is also shown as an adequate control of in vivo transduction.

With the development of the invention claimed herein, a research line is started to conduct gene therapy as an alternative for the treatment of chronic-degenerative illnesses, specifically liver cirrhosis in human beings, upon establishing an efficient vehicle to send genes to the liver, said genes producing therapeutic proteins that help reestablish the normal functions of the liver (see FIGS. 1 and 4), where it is shown how to deliver effectively and in an adequate way huPA gene to obtain the degradation of the excess collagens deposited through the over-expression of huPA protein.

Figure 2:
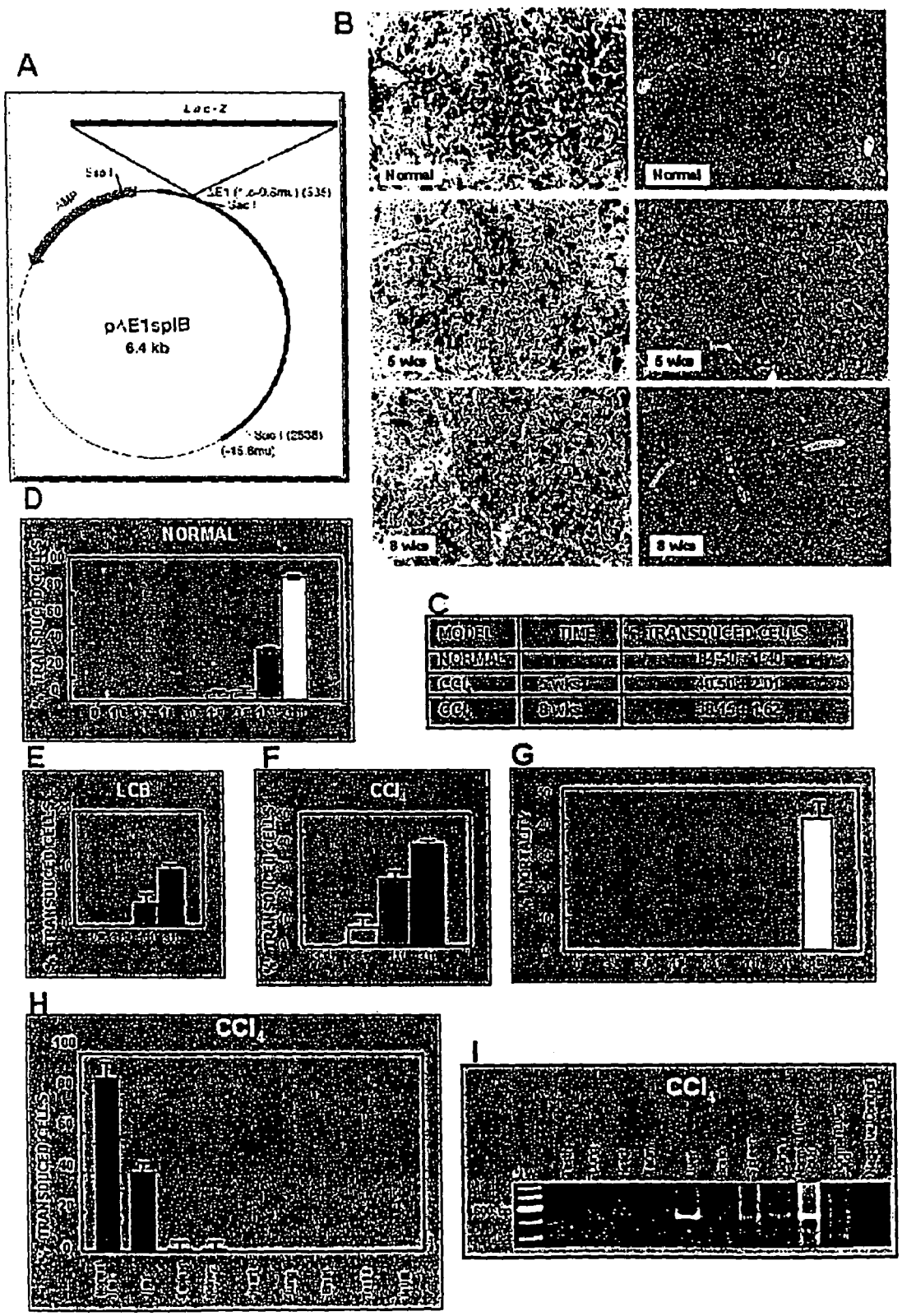
FIG. 2 shows the scheme of the adenoviral vector map containing the reporter gene LacZ (A) used to determine dose-response, safety, toxicity, and bio-distribution of an exogenous gene in several normal and cirrhotic laboratory rat organs (B-I)

In the left panel of FIG. 2B, frozen cuts are shown which are stained with X-gal. In the left panel of FIG. 2B tissues of the same livers on which a X-gal determination was conducted are shown, but said tissues were soaked in paraffin before being cut and were stained with Sirius Red in order to visualize the fibrosis grade. Transduction grade was about 40% in cirrhotic rats, compared to 84% in normal rats (FIG. 2C). Because the dose-response essay establishes a dose of $3 \times 10^{11}$ total viral particles (FIGS. 2D, E, and F), in FIG. 2H the adenoviral vector bio-distribution is shown and in the graph it can be seen that the main target organ is the liver, both in healthy rats as well as in rats receiving a chronic administration of $CCl_4$. Spleen and kidney presented a transduction grade under 1%. The adenoviral vector bio-distribution was corroborated by PCR, the primers use amplify a region of adenovirus and a region of reporter gene Lac-Z and the bands obtained (FIG. 2-I) in the different organs correspond to the distribution found with X-gal reaction. Finally, using the $3 \times 10^{12}$ viral particle dose, we found that about 50% of the animals died through disseminated intravascular coagulopathy.

The Modified huPA Produced is Intracellularly Located

Taking into account the well known uPA function as one of the main primers of the extracellular matrix proteolysis (ECM), and as plasmid activator and hepatocyte growth factor (HGF) (Kim, T. H., Mars, W. M., Stolz, D. B., Peterson, B. E., and Michalopoulos, G. K. Extracellular matrix remodeling at the early stages of liver regeneration in the art. Hepatology 1997:26:896-904; Mars, W. M. Zarnegar, R., Michalopoulos, G. K. Activation of hepatocyte growth factor by the plasminogen activators uPA and tPA. Am. J. pathol. 1993: 143:949-958. (35); and Roselli, H T., Su, M., Washington, K., Kerins, D. M., Vaughan, D. E. and Russel W. E. Liver regeneration is transiently impaired in urokinase-deficient mice. Am. J. Phisiol. 1998:275:G1472-G1479), it was decided to use human uPA to induce enzyme activity specifically in cirrhotic livers and to test its effect in fibrosis reversion. However, to avoid bleeding risk as a consequence of huPA secretion, we used a non secreted huPA form with a modification in the amino-terminus and carboxy-terminus ends to prevent to the greatest possible extent it secretion in the blood stream (FIG. 3A and 3B).

Figure 3:
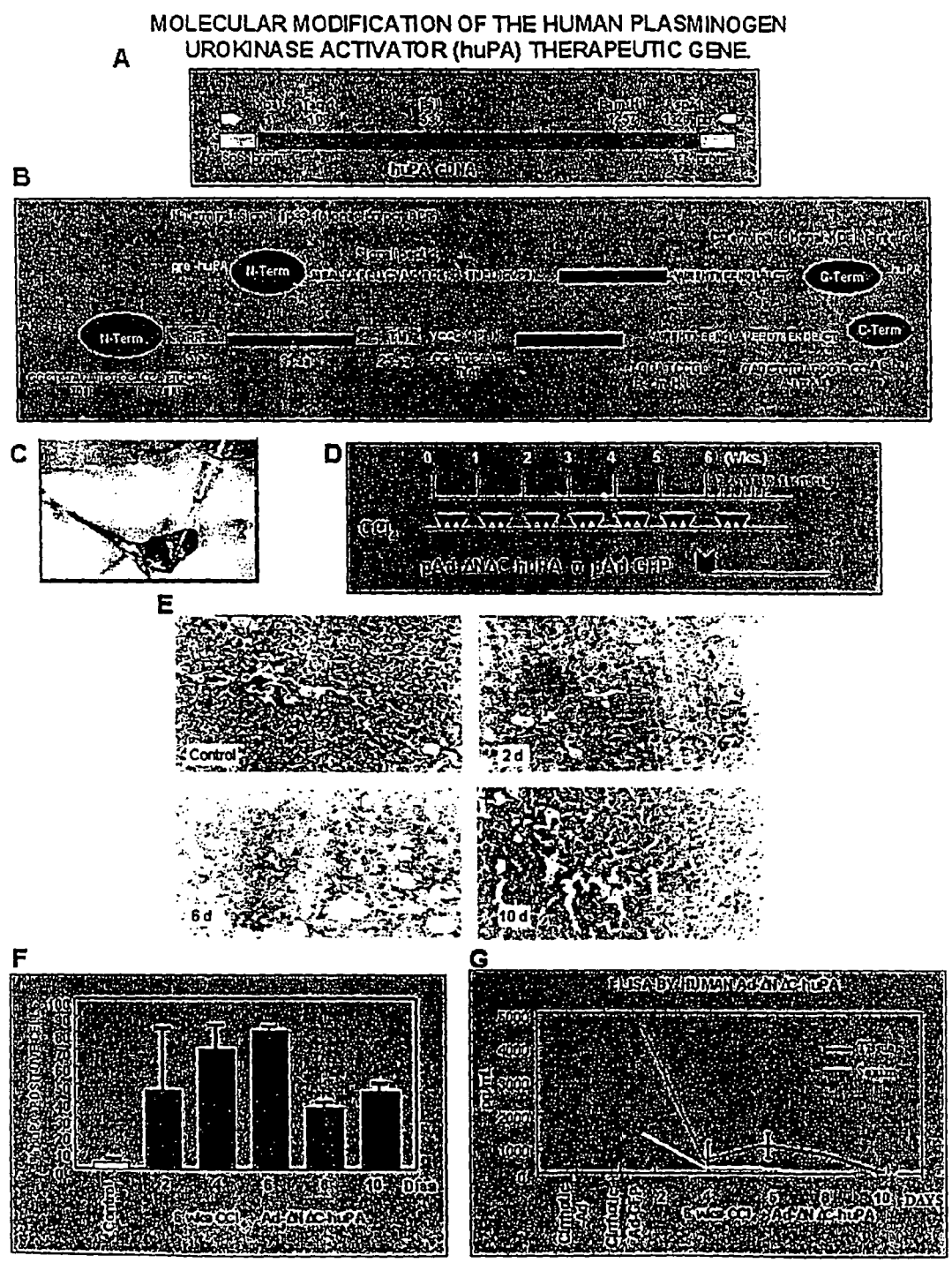
FIG. 3 is a scheme representation showing the genetic modification of human uPA cDNA and the formation of Ad-ΔNΔC-huPA (therapeutic) corresponding adenoviral vectors, the administration through the iliac vein (A-D). The determination of human huPA therapeutic protein expression levels in cirrhotic rats is also shown through corresponding immunohistochemistry and ELISA essays (E-G)

To induce cirrhosis, the rats received $CCl_4$, intraperitoneally, 3 times per week during six to eight weeks (FIG. 3D). After a six-week administration of $CCl_4$, various livers sections of cirrhotic animals injected with pAd-GFP and saline used as control were analyzed, and nodes of various sizes similar to human cirrhosis were observed. Thick and thin fibrosis bands were observed around the nodes with obvious parenchyma collapse and the typical collagen bridge pattern linking the portal tracts and central veins. Necrotic and swollen hepatocytes were frequently associated with the fibrosis bands (FIG. 4A). Thus, the pAd.PGK-ΔNΔC-huPA was used to treat the animals and revert severe fibrosis as well as stimulate hepatocytes regeneration. Based in the previous observation (García-Bañuelos J, Siller Lopéz, F, Aguilar-Córdova, E and Armendáriz-Borunda J. Adenovirus-Mediated gene delivery to cirrhotic rat livers: potential tool for gene therapy. Gene Ther. And Mol. Biol. Accepted 2000), the dose of $6 \times 10^{11}$ viral particles/kg of pAd.PGK-ΔNΔC-huPA adenoviral vector was established, administrated through the iliac vein in one dose at the end of the sixth week of $CCl_4$ chronic intoxication (Armendáriz-Borunda, J. Katai H., Jones, C. M., Seyer J. M., Kang J. M. and Ragliow R. Transforming growth factor β is transiently enhanced at a critical stage during liver regeneration following $CCl_4$ treatment. Lab Invest. 1993:69: 283-294). It is important to observe that $CCl_4$ damage continued in rats sacrificed two days after the administration of adenoviral vector (FIG. 3D). In other words, rats sacrificed on days 8 and 10 received three additional injections of hepatotoxic agent compared to the rest of the animals. After only one pAd.PGK-ΔNΔC-huPA injection and ELISA essay was conducted to determine the presence of huPA protein in liver homogenate and serum (FIG. 3G). The results showed that a large quantity of modified huPA protein was detected in the tissue extract, compared to the concentration detected in the sera, which can be explained by the fact that the produced protein leaves the damage hepatocytes. Importantly, huPA levels produced in said experiments were very high (~5 ng/ml) [100 times higher compared to other protein induction systems in similar experimental models (Schirmacher, P., Geerts, A., Jung., W., Pietrangelo, A., Rogler, C. E., Dienes, H. P. The role of Ito cells in the biosynthesis of HGF-SF in the liver. EXS 1993:65:28.5-299). (43)]. huPA levels increased by day 2, diminishing afterwards but showing detectable levels, compared to the lack of expression in control animals injected with irrelevant adenovirus, pAd-GFP (FIG. 3G). Besides, there are evidences that the modified huPA was located intracellularly when the detection was made by huPA immunohistochemistry with specific antibodies, showing and confirming the induction of said protein in cirrhotic livers (FIGS. 3E and F). Normal and cirrhotic rat liver tissues used as controls show occasionally hepatocytes stained with huPA antibody (~3.5%). Contrasting with this finding, the animals treated with pAd.PGK-ΔNΔC-huPA showed by day 2 a significant increase of huPA immunostained hepatocytes (46%) (FIGS. 3E and F), reaching a peak after day 6 on which over 80% of the cells were positives. Besides, Kupffer cells and biliary epithelium cells also showed immunoreactivity.

Figure 8:
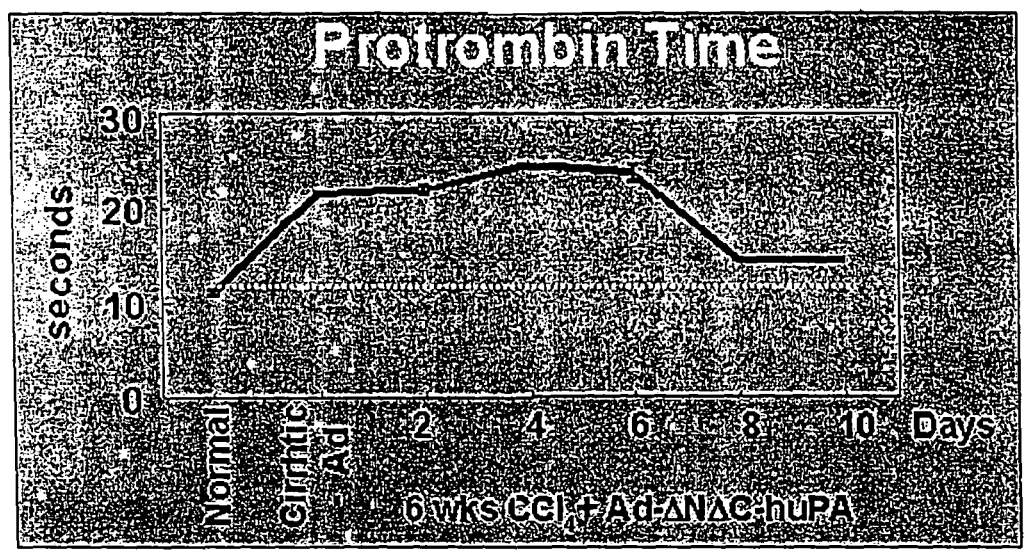
FIG. 8, (A) shows the prothrombrin times of rats sacrificed on different days after the administration of Ad-ΔNΔC-huPA vector o treated only with saline. Besides (B) shows the evaluation of liver weight/body weight×100 ratio to detect a possible liver hyperplasia and/or hypertrophy in these livers.
Figure 8:
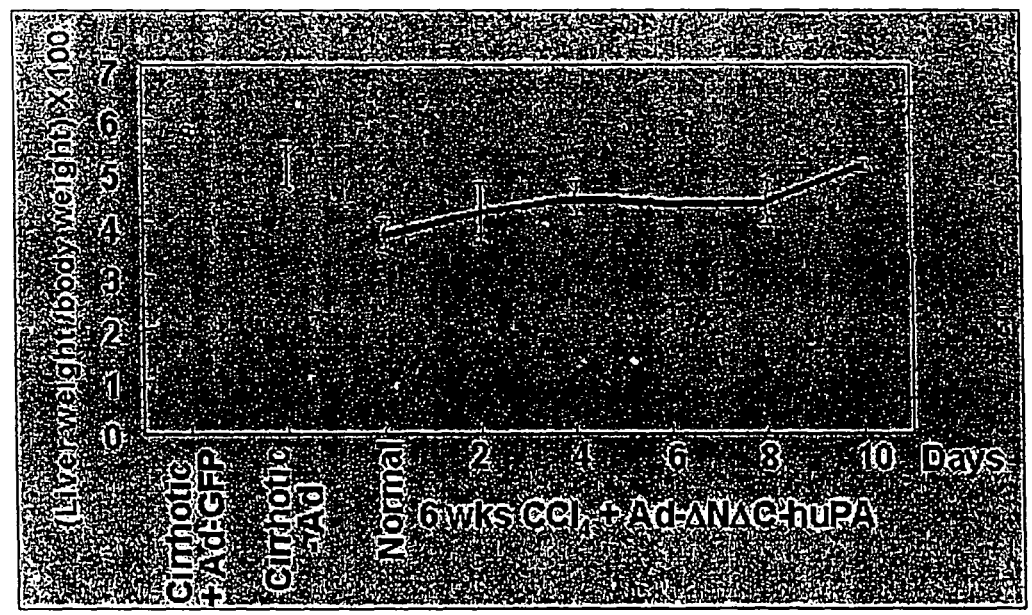

Even though the vector application induced a histological appearance of degenerate hepatocytes and there was an important serum transaminase increase in the first days after pAd-ΔNΔC-huPA treatment (table 1), said increase was transient and none of the animals died of liver failure as a consequence are overlain adenoviral hepatitis. Compared to cirrhotic control animals that received saline (n=5) and an irrelevant adenovirus preparation (pAd-GFP) (n=5), the animals injected with pAd.PGK-ΔNΔC-huPA showed a remarkable improvement in liver function tests (table 1). Globally, the rats sacrificed in the last days showed prothrombin times (PT) of 14 seconds (very similar to normal values) 8 and 10 days after the adenovirus administration compared to 24 seconds on days 2, 4 and 6 (FIG. 8A). Importantly, no anemia was observed, but a transitory small decrease of platelets (table 2) in animals that received pAd.PGK-ΔNΔC-huPA could be seen. With regard to this point, it has previously been reported that the injection of adenoviral vectors in normal animals induces a transitory platelet decrease (Brann, T., Kayda, D., Lyons, R. M., Shirley, P., Ruy, S., Kaleko, M., and Smith, T. Adenoviral vector-mediated expression of physiologic levels of human factor VIII nonhuman primates. Hum. Gene Ther. 1999:10:2999-3011).

TABLE 1

SUMMARY OF GROUP AVERAGES OF LIVER FUNCTION TEST RESULTS

| | GROUP | DAYS | | | | |
|---|---|---|---|---|---|---|
| | | 2 | 4 | 6 | 8 | 10 |
| ALT (IU/L) | Normal | 73.6 ± 10.9 | | | | |
| | pAd-ΔNΔC-huPA | 1563 ± 948.8 | 443.75 ± 308 | 345 ± 60 | 88.5 ± 24.7 | 684 ± 50 |
| | pAd-GFP | 890 ± 260.2 | 337.5 ± 54.4 | 426 ± 48 | 410 ± 45 | 715 ± 60 |
| AST(IU/L) | Normal | 162.3 ± 30.9 | | | | |
| | pAd-ΔNΔC-huPA | 1590 ± 957.09 | 676.5 ± 576.3 | 395 ± 70 | 137 ± 29.7 | 599 ± 30 |
| | pAd-GFP | 737 ± 156.98 | 627.5 ± 389.6 | 2100 ± 114 | 2250 ± 55.6 | 2315 ± 115.3 |
| Alcaline phosphatase (IU/L) | Normal | 159.7 ± 34.7 | | | | |
| | pAd-ΔNΔC-huPA | 525.7 ± 11.3 | 385.2 ± 221.7 | 336 ± 40 | 205 ± 54.5 | 310 ± 28.5 |
| | pAd-GFP | 382.5 ± 40.3 | 715 ± 181 | 577 ± 63.4 | 454 ± 46.5 | 485 ± 45.3 |
| Bilirrubine total (mg/dL) | Normal | 0.55 ± 0.07 | | | | |
| | pAd-ΔNΔC-huPA | 0.97 ± 0.6 | 0.825 ± 0.43 | 0.6 ± 0.2 | 0.94 ± 0.3 | 0.7 ± 0.3 |
| | pAd-GFP | 0.35 ± 0.07 | 0.75 ± 0.6 | 2.3 ± 0.4 | 1.4 ± 0.3 | 1.2 ± 0.2 |

TABLE 2

SUMMARY OF THE AVERAGES PER GROUPS OF HEMATOLOGY RESULTS

| | GROUP | DAYS | | |
|---|---|---|---|---|
| | | 2 | 4 | 6 |
| Hemoglobin (g/dL) | Normal | 13.5 ± 0.64 | | |
| | pAd-ΔNΔC-huPA | 13.5 ± 1.77 | 15.5 ± 0.8 | 16.5 ± 0.14 |
| | pAd-GFP | 14.9 ± 1.13 | 14 ± 1.12 | 14.1 ± 0.99 |
| Hematocrite (%) | Normal | 40.6 ± 0.85 | | |
| | pAd-ΔNΔC-huPA | 40.1 ± 5.87 | 46.5 ± 0.7 | 49.5 ± 0.25 |
| | pAd-GFP | 40.3 ± 0.07 | 41.9 ± 2.3 | 42.4 ± 2.83 |
| Erythrocytes ($10^6$/mm$^3$) | Normal | 6.95 ± 0.226 | | |
| | pAd-ΔNΔC-huPA | 7.1 ± 1.2 | 6.99 ± 0.56 | 7.5 ± 0.7 |
| | pAd-GFP | 7.14 ± 0.226 | 7.7 ± 0.93 | 7.3 ± 0.51 |
| Leucocyte ($10^3$/mm$^3$) | Normal | 2.47 ± 1.79 | | |
| | pAd-ΔNΔC-huPA | 5.6 ± 2.08 | 4.96 ± 2.9 | 8.9 ± 2.2 |
| | pAd-GFP | 6.8 ± 0.99 | 9.43 ± 1.2 | 11.3 ± 6.7 |
| Lymphocyte (%) | Normal | 45.5 ± 12.6 | | |
| | pAd-ΔNΔC-huPA | 41.7 ± 0.99 | 55.4 ± 1.3 | 49.8 ± 2.8 |
| | pAd-GFP | 44.9 ± 1.01 | 61.7 ± 4.5 | 50.7 ± 27.08 |
| Neutrophiles (%) | Normal | 46.2 ± 7.99 | | |
| | pAd-ΔNΔC-huPA | 53.9 ± 3.18 | 41.4 ± 2.5 | 49.2 ± 3.2 |
| | pAd-GFP | 49.8 ± 2.5 | 37 ± 3.5 | 47.1 ± 27 |
| Monocytes (% + −) | Normal | 1.5 ± 1.75 | | |
| | pAd-ΔNΔC-huPA | 3.1 ± 4.23 | 1.33 ± 1.22 | 0.2 ± 0.02 |
| | pAd-GFP | 3.9 ± 5.24 | 0.24 ± 2.3 | 0.3 ± 0.35 |
| Platelets ($10^3$/mm$^3$) | Normal | 1050 ± 45.6 | | |
| | pAd-ΔNΔC-huPA | 959.5 ± 78.5 | 859 ± 52.3 | 1020.5 ± 38.9 |
| | pAd-GFP | 896 ± 80.6 | 961 ± 79 | 693 ± 127 | huPA Over-expression in Liver Induces Fibrosis Reversion

Figure 5:
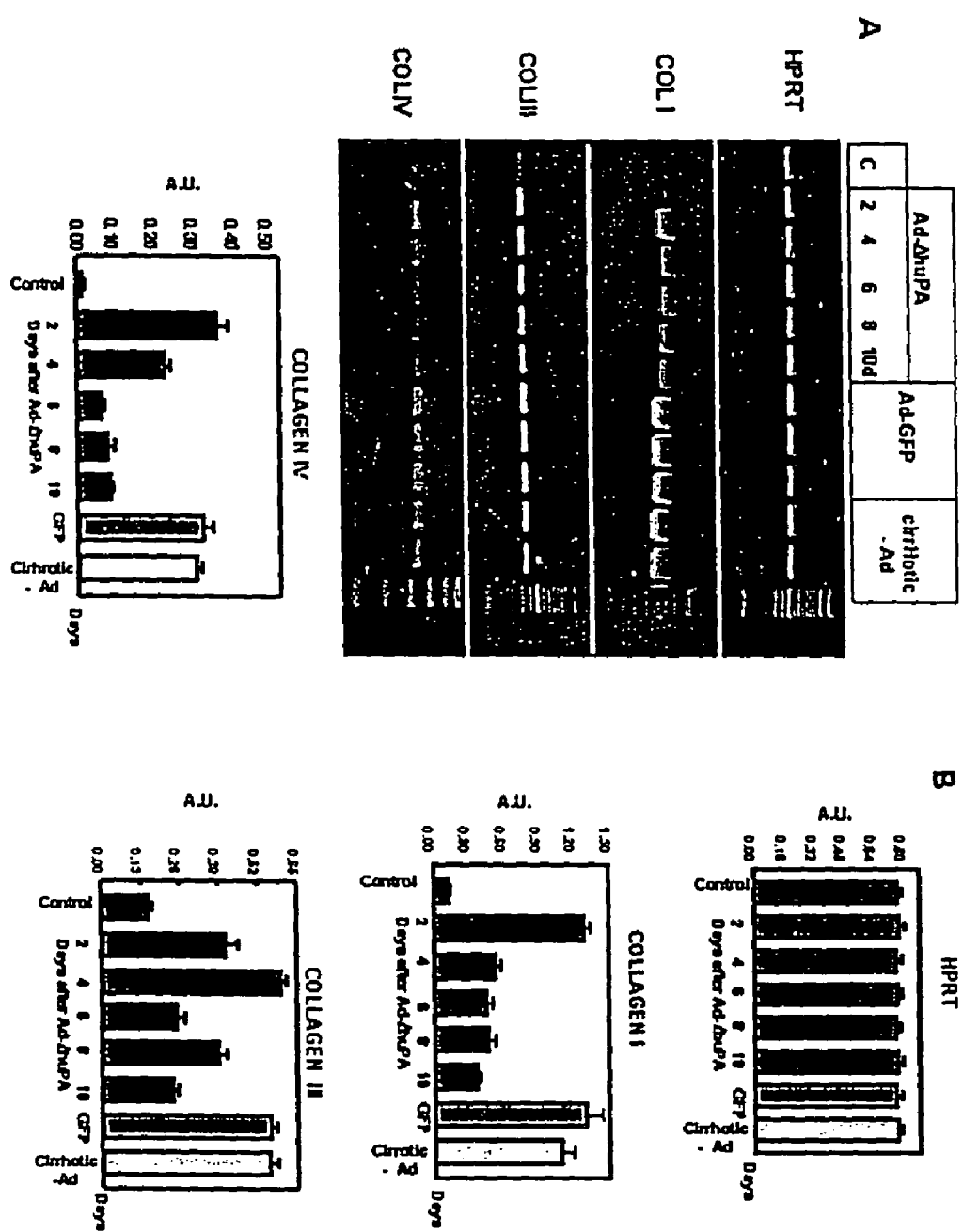
FIG. 5 shows the semi-quantitative analysis through reverse transcriptase polimerase chain reaction (RT-PCR) of the messengers RNA for collagens types I, III, and IV of the livers of cirrhotic rats treated with the adenoviral vector Ad-ΔNΔC-huPA, Ad-GFP or only with saline in which amplified PCR products are shown corresponding to said genes (A), and their corresponding densitometrical determination compared to the expression of a constitutive expression gene (B)
Figure 6:
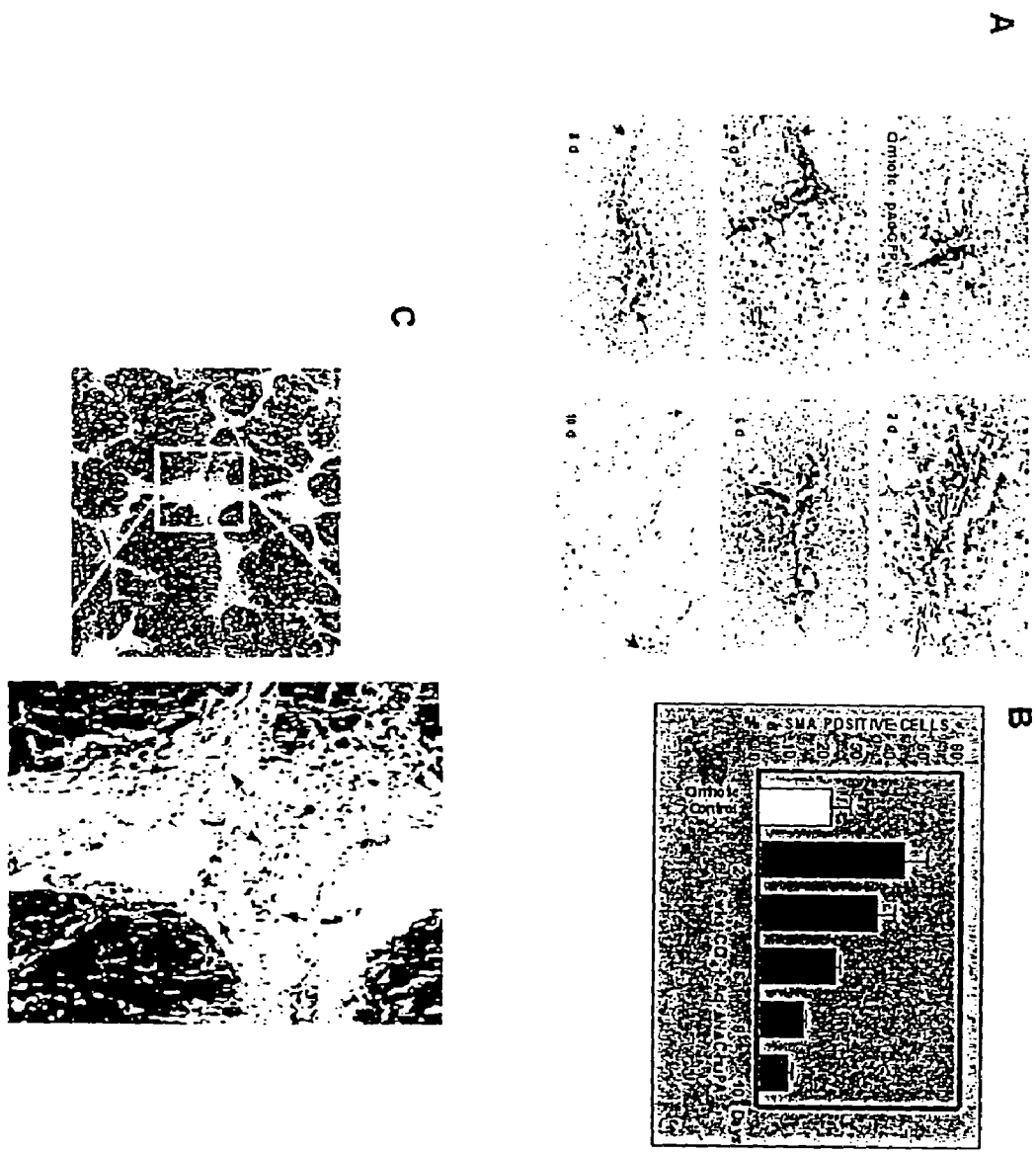
FIG. 6 shows the immunohistochemical staining of rat cirrhotic livers with anti α-SMA (smooth muscle actin) antibody after the delivery of Ad-ΔNΔC-huPA (A), therapeutic vector, as well as the quantitative computing through a computer assisted morphometrical analysis of the percentage of α-SMA positive cells (B); and (C) a magnified view of α-SMA positive cells.

Besides its plasminogen activation role, huPA is considered one of the main primers leading to the activation of the cascade of metalloproteases associated to the extracellular matrix degradation (Kim, T. H., Mars, W. M., Stolz, D. E., Petersen, B. E., and Michalopoulos, G. K. Extracellular matrix remodeling at the early stages of liver regeneration in the rat. Hepatology 1997: 26:896-904). After activating plasminogen in plasmin, uPA also activates procolagenases and possibility other metalloproteases (MMPs) converting them into the active form at early stages (Steler-Stevenson, W. G. Dynamics of matrix turnover during pathologic remodeling of the extracellar matrix. Am. J. Pathol. 1996:148:1345-1350. (33)). Thus, we determined first the fibrosis grade in cirrhotic livers stained with Masson. Computer assisted morphometrical analysis of multiple fields showed that rats treated with pAd.PGK-ΔNΔC-huPA presented a dramatic fibrosis reduction by day ten (85%) (FIGS. 4B and B'), compared to fibrosis levels at the beginning of the treatment, as well as compared to cirrhotic animals receiving pAd.GFP (FIGS. 4A and A') and only saline. Said findings are consistent with the data showed on FIGS. 4C and C' where metalloprotease-2 (MMP-2) activity in liver homogenates was quantitatively determined through a specific ELISA essay. Said essay detects active MMP-2 levels (Verheijen, J H, Nieuwenbroek, N M, Beekman B, Hanemaijer, R, Verspaget H W, Ronday H K, Bakker A H. Modified proenzymes as artificial substrates for proteolytic enzymes: colorimetric assay of bacterial collagenase and matrix metalloproteinase activity using modified pro-urokinase. Biochem J. 1997:323 (Pt3): 603-609), which specifically degrades type IV collagen and, to a lesser extent, other collagens (Corcoran, M L, Hewitt, R E, Kleiner, D E Jr., Stetler-Stevenson, W G. MMP-2: expression, activation and inhibition, Enzyme protein 1996:49(1-3):7-19; Nogase, H., Ogata, Y, Suzuki, K, Enghild, J J, Salvensen G. Substrate specific and activation mechanisms of matrix metalloproteinases. Biochem. Soc. Trans. 1991(3)715-8). A six-fold MMP-2 increase was found (above 11.5 ng/ml) four days after huPA administration compared to normal rats and a three-fold increase was observed compared to control cirrhotic animals. On the other hand, and independently from the induction of specific huPA collagens and the physiological importance of collagen degradation activity, the expression of type I, II and IV endogenous collagen genes was evaluated through semi-quantitative RT-PCR, which permitted to detect specific changes in the baseline levels of said genes. The expression of type IV collagen gene presented ~5-fold decrease by day six and the expression of type I collagen gene presented a four-fold decrease by day 10 in rats that received pAd.PGK-ΔNΔC-huPA compared to the rats that received an irrelevant adenovirus, pAd-GFP. Type III collagen expression diminished ~2 times on day 10 of injection of huPA adenoviral vector compared to pAd-GFP (FIGS. 5A and B). Said data strongly suggest that the over-expression of human huPA induces the turning off of said genes that code for ECM proteins. In cirrhotic livers with severe fibrosis, hepatic stellate cells (HSC, main collagen producing cells) are increased in fibrotic areas, and most of them change their phenotype to activated HSC that specifically express alfa-smooth muscle actin (α-SMA) (Nyberg-Hoffman, C., Shabram, P., Li, W., Giroux, D. and Aguilar-Cordova, E. Sensitivity and reproducibility in adenoviral infectious titer determination. Nature Med. 1997:3(7):808-11). α-SMA expression was examined in rat livers through immunohistochemistry and it was discovered that it correlates to the distribution of excess ECM deposited throughout liver parenchyma, results that are consistent with the % of fibrotic tissue. There is a significant reduction in the number of α-SMA positive cells (8.9% on day ten compared to 43.2% on day 2 after the treatment) (FIGS. 6 A and B). Besides, a representative fibrosis area is magnified, where the HSC are clearly visible (FIG. 6C).

HuPA Induces a Vigorous Cirrhotic Liver Cell Regeneration

Figure 7:
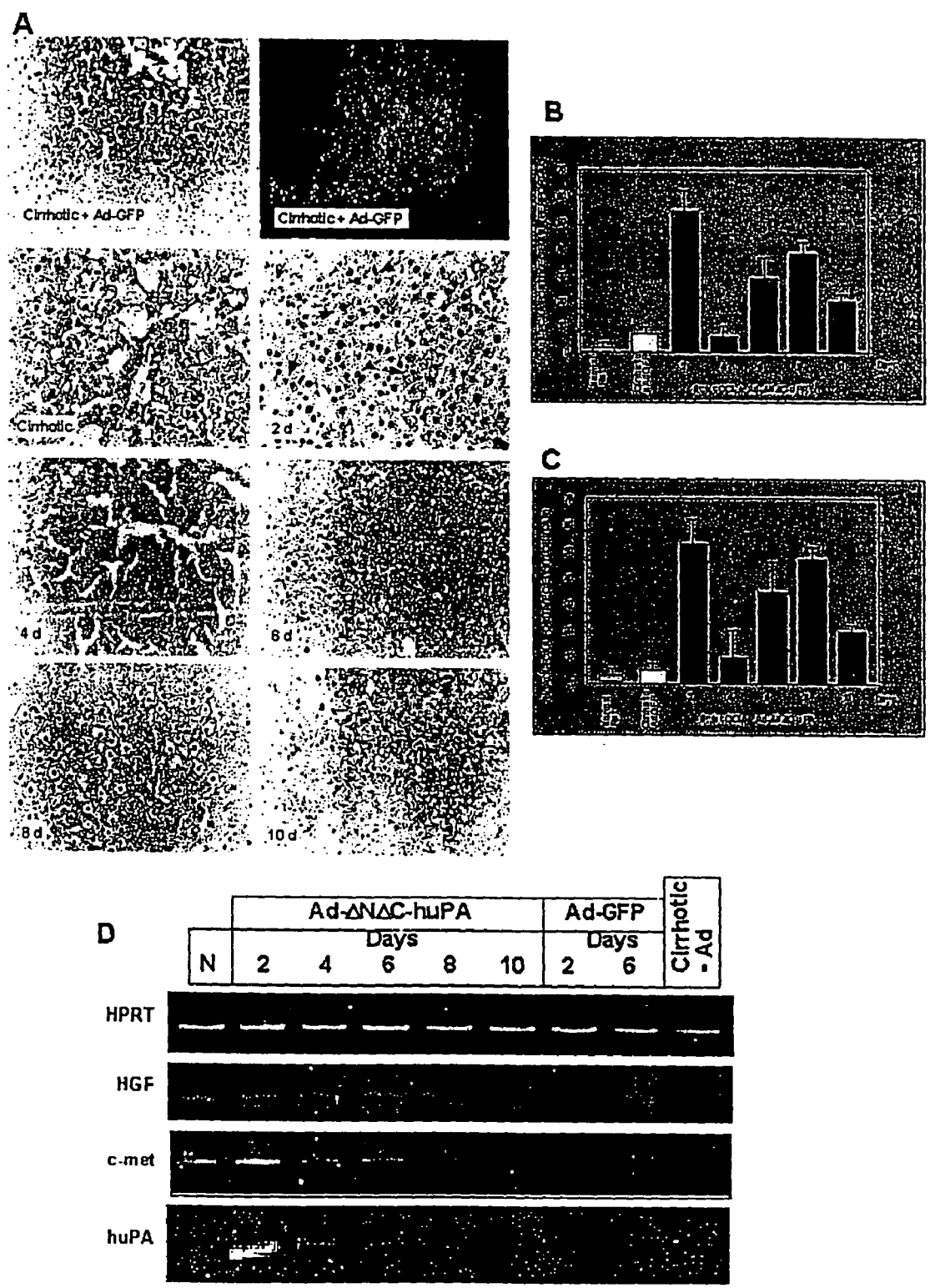
FIG. 7 shows the immunohistochemical staining of cirrhotic rat liver sections with anti-PCNA (Proliferating Cell Antigen) antibody to evaluate hepatocytes proliferation after the administration of Ad-ΔNΔC-huPA adenoviral vector, Ad-GFP o saline only (A); (B) and (C) show the percentage of immunostained cells in the periportal and lobular region, respectively, through an automated image analyzer. (D) shows the semi-quantitative RT-PCR determination of hepatocyte growth factor (HGF), c-met and huPA after the administration of different vectors in which the PCR amplified products corresponding these genes are shown.

Having solved the first half of the process, we proceeded to determine the liver regeneration level "necessary to refill the empty spaces" after conducting extracellular matrix degradation (ECM). FIG. 7 represents mitosis kinetics in livers, probably stimulated by in situ HGF activation (Locaputo, S., Carrick, T. L and Bezerra, J. A. Zona Regulation of gene expression during liver regeneration of urokinase transgenic mice. Hepatology 1999:291106-1113). Hepatocyte proliferation was measured as the percentage of stained cells with a specific antibody against proliferation cellular nuclear antigen (PCNA). The number of PCNA positive hepatocytes was dramatically higher (10 times) in livers of rats treated with pAd.PGK-ΔNΔC-huPA compared to livers of rats treated with pAd-GFP and normal livers (FIG. 7A). The marking index showed that about 55% of hepatocytes were positively stained with anti-PCNA antibodies both in periportal areas (FIG. 7B) and in centrilobular areas (FIG. 7C) (Hattori, N., Sisson, T. H., Xu, Y., and Simon R. H. Upregulation of fibrinolysis by adenovirus-mediated transfer of urokinase-type plasminogen activator genes to lung cells in vitro-and in vivo. Hum. Gene Ther. 1999:10:215-222) 2 days after pAd.PGK-ΔNΔC-huPA injection together with numerous mitotic figures and binucleated hepatocytes (FIG. 7A). Marking indexes of 40% were detected even 8 days after the adenoviral vector administration (FIGS. 7B and C). The positive cells detected by day 10 indicate a re-establishment of the liver functional mass, which was confirmed through the clear normalization trend (Table 1 and FIG. 8A) shown by means of livers function tests (AST, ALT, Bilirubin and prothrombin times).

HGF is one of the most potent hepatocytes mitogens (Michalopoulos, G. K. HGF in liver regeneration and tumor promotion. Prog Clin. Biol. Res. 1995:391:179-185) and c-met is its corresponding tirosine kinase receptor transducing its signal. FIG. 7D shows an over-expression of HGF gene in animals treated with huPA and only a minor expression in cirrhotic control animals and pAd-GFP treated animals. Said over-expression of this gene is most notable in c-met 2 days after huPA administration which suggest that liver cell proliferation is controlled through this mechanism.

Finally, the liver weight related to body weight of the animals was measured at the time when the animals were sacrificed to determine a possible uncontrolled growth (FIG. 8B). As can be observed, there was only a very small increase in the weight of the organ by day 10, suggesting that no "abnormal" cell growth regulating mechanism is involved.

The preferred way to apply the present invention is through endovenous administration of the recombinant adenoviral vectors (or any previously mentioned vector containing the therapeutic genes) of the instant invention, in which therapeutically effective amount is administered with a unitary dose regimen convenient to a fibrotic individual. This regimen can be adjusted according to the affliction degree. Generally, unitary doses of about $10^7$ to $10^{14}$ viral particles per individual are employed.

The preparation of a pharmaceutical compound including the adenoviral recombinant vectors of this invention can be made through the employment of standard techniques very well known by the persons skilled in the art, in combination with any of the pharmaceutically acceptable carriers described in the state of the art, including without restriction, starch, glucose, lactose, saccharose, gel, malt, rice, wheat flour, chalk, silica-gel, magnesium stearate, sodium stearate, glyceril monostearate powder, NaCl, glycerol, propilene glycol, water, ethanol, and similar. These compounds can take the pharmaceutical form of solutions, suspensions, pills, tablets, capsules, powders and slow release formula, and similar.

The above description and the following examples have the purpose to illustrate particular embodiments of the invention and they should not be considered as limitations of the scope of this patent.

EXAMPLES

Methodology to Demonstrate huPA Activity on Fibrosis Reversion and Liver Regeneration Stimulation a) Experiment Animals Mimicking Human Liver Cirrhosis The model consisted of animals submitted to $CCl_4$ chronic intoxication (Armendáriz-Borunda, J. Seyes, J. M., Kang, A. H. and Ranghow, R. Regulation of TGF gene expression in rat liver intoxicated with carbon tetrachloride. FASEB J. 1990: 4:215-221) in which liver cirrhosis is established since the sixth week of $CCl_4$ intraperitoneal administration (FIG. 3D) and that resembles human liver cirrhosis induced by alcohol abuse or chronic hepatitis C virus infection. Animals weighting 80 g received 3 intraperitoneal weekly doses of $CCL_4$-mineral oil mixture 1:6 during the first week, 1:5 during the second week, 1:4 during the third week and 1:3 during the weeks four to eight. Rats were paired to be used as control injecting them similarly only with the carrier. All the experimental methods have been previously described (García-Buñuelos J., Siller-López, F, Aguilar-Córdova, E. and Armendáriz-Borunda J. Adenovirus-mediated gene delivery to cirrhotic rat livers: potential tool for gene therapy. Gene Ther. and Mol. Biol. Accepted 2000), and all the adenovirus applications were conducted through the iliac vein (FIG. 3C).

b) Expression Vectors Containing Reporter Genes

Ad5-βGal adenoviral vector (FIG. 2A) comes from pΔE1sp1B, to which bacterial β-galactosidase gene (lac-Z) was inserted. β-Gal activity visualization was obtained with X-gal reagent which, in presence of β-galactosidase enzyme changes from colorless to blue. At the same time, the same Ad5-βGal batch was administrated to healthy rats (n=5) and cirrhotic rats. (n=5), after 5 and, 8 weeks of $CCl_4$ intoxication. The animals were sacrificed 72 hours after Ad5-βGal. For histological analysis and the determination of the expression of β-galactosidase (β-gal) protein coded for by the recombinant adenovirus, different organs were extracted: liver, spleen, heart, lungs, kidneys, brain, testes and ileum. Said organs were frozen at −30° C. and cut with a cryostat to obtain 8 μm sections. The cuts were exposed to X-gal reagent during 16-18 hours, counterstaining with Neutral Red. The percentage of transduced cells was determined through computerized image analysis in several fields. Cirrhotic rat liver cuts were also made, said cuts were soaked in paraffin, cut and stained with Sirius Red, which specifically stains collagen.

c) Adenoviral Vectors Containing huPA Therapeutic Gene

An adenoviral vector was constructed with the insertion of the cDNA coding for the totally functional non-secreted human urokinase plasminogen activator (pAd.PGK-ΔNΔC-huPA). Retention signals were added to the protein in endoplasmic reticulum (RE) in the amino-terminal and carboxi-terminal end in order to prevent the hemorrhage risk secondary to huPA secretion. Generally, proteins secreted are first translocated through the endoplasmic reticulum membrane and then are carried in vesicles to the Golgi apparatus. In the case of uPA, the translocation through the endoplasmic reticulum membrane is activated by a characteristic signal in the amino-terminus of the precursor protein. Said signal peptide is cut by signal peptidases during polypeptide transfer through the membrane. To inhibit or diminish uPA secretion in systemic circulation, the protein was modified in such a way that it was necessary to avoid its export from the endoplasmic reticulum. Human uPA cDNA (1,326 bp) cloned in pGEM3 in Xba I/Asp 718 sites (FIG. 3A) was modified in the carboxi-terminal end adding a sequence coding for KDEL signal (a highly conserved sequence characteristic of soluble proteins residing in RE lumen) besides residues upstream through the cloning of 75 nucleotides generated by PCR (FIG. 3B). To modify the amino-terminus, the 25 amino-terminal amino acids including the pre-uPA peptidic signal were replaced by an amino-terminal retention signal (RR) together with the "anchor" in the transmembrane region (TM) separated by a peptide spacer (31 a.a.) coming from the transmembrane II protein lip33 obtained through PCR (FIG. 3B). The RR sequence is constituted by arginine residues MHR-RRSR located near the transmembrane anchor region (TM) and are present in type II transmembrane protein as the invariable chain protein lip33. This resulting modified huPA gene was cloned in the adenoviral plasmid pAd.PGK-ΔNΔC-huPA, for the subsequent production of recombinant adenoviral vectors (ATCC Deposit No. PTA-10622). The preparation of said adenoviral vector was monitored to discard endotoxin in microplasm contamination. The reason for the use of this vector is the advantage that, because it does not secrete huPA, it does not cause hypocoagulation, or spontaneous bleeding, which is the main this disadvantage in cirrhotic animals. The PAd-GFP vector used here is an adenoviral vector deleted in E1 and E3 regions replication deficient previously described (Nyberg-Hoffman, C., Shabram, P., Li, W., Giroux, D. and Aguilar-Cordova, E. Sensivity and reproducibility in adenoviral infectious titer determination. Nature Med. 1997:3(7):808-11). The two vectors were produced under sterile laboratory conditions implemented to obtain totally characterized vectors. The vectors were titled and characterized (Nyberg-Hoffman, C., Shabram, P., Li, W., Giroux, D. and Aguilar-Cordova, E. Sensivity and reproducibility in adenoviral infectious titer determination. Nature Med. 1997:3(7):808-11) and batches were obtained with viral particle title (vp) to infection units (IU) ratio≧30.

d) Liver Homogenate Preparation for the Detection of huPA Therapeutic Protein Production and Metalloprotease Activity The rats were sacrificed as indicated in FIG. 3D and liver homogenates were prepared from 150 mg of tissue as described (Gao, C., Jokers, R., Gondipalli, P., Cai, S. H., Kennedy S. and Ponder K. P. Intramuscular of an hepatic transduction with a retroviral vector in mice. Hum. Gene Ther. 1999:10:911-922) and kept at −70° C. At the same time, serum samples were obtained and kept at −20° C. In summary, for huPA and in presence of protease inhibitors, 150 mg of liver were obtained and macerated in 400 μl homogenate buffer (0.05 M Tris-HCl, 0.15 M NaCl, 0.01 M HEPES, 2 mM $CaCl_2$, 0.01% Tween 80, 1 mM phenylmethylsulfonyl fluoride (PMSF), pH 8.5). The homogenate was centrifuged at 12,000×g during 15 minutes and huPA levels were determined through ELISA in supernatant using a commercially available kit (Biopool, Sweden) consisting of a specific enzyme immunoessay for human uPA quantitative determination. The essay sensitivity detects uPA antigen baseline levels in 0-5 ng/mL linear range. The total protein levels were determined using Bradford technique for protein quantification (Bradford, M. M A rapid and sensitive method for the quantification of microgram quantities of protein utilizing the principle of protein-dye binding. Anal. Biochem. 1976:72: 248-54). For MMP-2 essay the samples were homogenized using a homogenizer (Politron PT 3000, Kinematica AG, Brinkman, Switzerland) during 5 minutes at 8,000×g in 4 ml 0.15 M NaCl, at 4° C. After 3 cycles of freezing-thawing they were sonicated twice at 21 kilocycles per second during 1 minute at 4° C. and centrifuged at 8,000×g during 10 minutes at 4° C., aliquoted and kept at −70° C. MMP-2 levels were determined in said supernatants through ELISA using a commercial kit (Biotrak, Amersham).

e) Biochemical Evaluation of Liver and Blood Functional Tests

Blood was taken from the animals at specific times and liver functional tests were conducted in serum (ALT, AST, alkalinephosphatase and bilurubin) in an automated apparatus (Synchron Cx7). Prothrombin times were analyzed on plasma with an automated device (ACL-3000) and blood analyses were conducted with another automated device (Cell-Dyn 3500R).

f) Histological and Immunohistochemical Evaluation of Liver Sections

The rats were sacrificed on days 2, 4, 6, 8 and 10 after pAd.PGK-ΔNΔC-huPA administration (FIG. 3D). A group of cirrhotic animals that received pAd-GFP (irrelevant adenovirus) and a group of cirrhotic animals that received a saline were used as control groups. At least five rats were included in each group. For the histological study, the livers obtained were immediately fixed through immersion in 10% formaldehyde in phosphate buffer (PBS), dehydrated in ethyl alcohol and soaked in paraffin. The 5μ thick cuts were stained with hematoxylin/eosin, Sirius Red and Masson trichromic stain and in this last experiment fibrosis percentage was determined in the affected livers using a computerized image analyzer (Qwin Leica) through the random analysis of 10 fields per slide and calculating the connective tissue ratio to total liver area. For the immunohistochemistry, liver sections were mounted on silanized slides, paraffin was removed and the endogenous peroxidase activity was blocked with 0.03% $H_2O_2$ in absolute methanol. They were incubated overnight at room temperature with monoclonal antibodies against PCNA (Proliferation cellular nuclear antigen) and smooth muscle α-actin (Boehringer Mannheim, Ger) diluted with PBS 1/20 and 1/50, respectively, and with antihuman uPA goat polyclonal antibody (Chemicon International, USA) diluted in PBS 1/400. The reaction was detected with peroxidase marked rabbit or goat polyclonal antibodies, developed with diaminobenzidine, and counterstained with hematoxyllin. Four fields were randomly evaluated for quantification purposes from intralobular and periportal areas. Positive and negative cells were counted with an automated image analyzer (Qwin, Leica) and data were expressed as positive cell percentage. The histopathological analysis was interpreted by two independent certified pathologists with a 5% difference margin.

g) RNA Extraction and Semi-quantitative RT-PCR

Total RNBA was immediately isolated after obtaining the livers in the defined times, according to Chomczynski and Sacchi's method (Chomczynski, P. and Sacchi, N. Single-step method of RNA isolation by acid guanidinium thiocyanato-phenol chloroform extraction. Anal. Biochem. 1987: 162:156-159). Liver tissue was homogenized through a Politron device in presence of Trizol and then chloroform was added obtaining an aqueous phase and precipitating RNA with isopropanol. RNA quantity was determined through spectrophotometry at 260/280 nm. The quality was verified through 1% agarose gel and formaldehyde electrophoresis.

Analysis of HGF (Hepatocyte Growth Factor) gene expression, c-met (HGF cellular receptor) and collagens were conducted through semi-quantitative RT-PCR. We used a methodology developed in our laboratory and described in Delgado-Rizo et al, (Delgado-Rizo, V., Salazr, A, A. Panduro, A., Armendáriz-Borunda, J. Treatment with anti-transforming grown factor β antibodies influences an altered pattern of cytokines gene expression in injured rat liver. Biochim. Biophys, Acta 1998: 1442:20-27). Briefly, the livers of at least 3 animals in each group were processed. In the same way, 3 different RT-PCR reactions were conducted on each liver, and quantitative densometrical results of their averages are shown. The amplified genes were:

| GENE | PRIMERS | AMPLIFIED FRAGMENT | |
|---|---|---|---|
| HGF | (sense) 5'ATGCTCATTGGACCCTGGT3' | 700 bp | SEQ ID NO. 1 |
| | (antisense) 5'GCCTGGCAAGCTTCATTA3' | | SEQ ID NO. 2 |
| c-met | (sense) 5'CAGTGATGATCTCAATGGGCAAT3' | 726 bp | SEQ ID NO. 3 |
| | (antisense) 5'AATGCCCTCTTCCTATGACTTC3' | | SEQ ID NO. 4 |
| Collagen I | (sense) 5'CAAGAATGGCGACCGTGGTGA3' | 1043 bp | SEQ ID NO. 5 |
| | (antisense) 5'GGTGTGACTCGTGCAGCCATC3' | | SEQ ID NO. 6 |
| Collagen III | (sense) 5'AGATGGATCAAGTGGACATC3 | 449 bp | SEQ ID NO. 7 |
| | (antisense) 5'CATGTTTCTCCGGTTTCCAT3' | | SEQ ID NO. 8 |

The previously isolated RNA was underwent reverse transcription through enzyme (M-MLV) and the obtained cDNAs were submitted to amplification in a thermocycler under the following conditions: 5 minutes at 94° C., 1 minute at 60° C. and 1.5 minutes at 72° C. during 30 cycles. The expression levels of all the transcripts were normalized with a HPRT constitutive expression gene.

The hepatocyte growth factor (HGF) has multifunctional activities including cell proliferation, migration and differentiation (Kim, T. H., Mars, W. M., Stolz, D. B., Petersen B. E. and Michalopoulos, G. K. Extracellular matrix remodeling at the early stages of liver regeneration in the rat. Hepatology 1997:26:896-904; and Michalopoulos, G. k., DeFrances M. C. liver regeneration. Science 1997:276:60-66). In the normal liver, HGF is produced by hepatic stellate cells (HSC) (Schirmacher, P., Geerts, A., Jung, W., Pietrangelo, A., Rogler, C. E., Dienes, H. P. The role of Ito cells in the biosynthesis of HGF-SF in the liver. EXS 1993:65:285-299) and is sequestered in the extracellular matrix (ECM) (Liu, M. L. Mars, W. M., Zarnegar, R., Michalopoulos, G. K., Uptake and distribution of hepatocyte growth factor in normal and regenerating adult rat liver. Am. J. Pathol. 1994:144:129-140). Moreover, HGF is also produced by the placenta, lung and brain (Schirmacher, P., Geerts, A., Jung, W., Pietrangelo, A., Rogler, C. E., Dienes, H. P. The role of Ito cells in the biosynthesis of HGF-SF in the liver. EXS 1993:65:285-299 and Wolf, H. K., Zarnegar, R. Michalopoulos, G. K. Localization of hepatocyte growth factor in human and rat tissues: an immunohistochemical study. Hepatology 1991:14488-494). It has been reported that uPA can activate single chain HGF (scHGF, inactive form), twin chain HGF (tcHGF, active form) (Schirmacher, P., Geerts, A., Jung, W., Pietrangelo, A., Rogler, C. E., Dienes, H. P. The role of Ito cells in the biosynthesis of HGF-SF in the liver. EXS 1993:65:285-299 and Wolf, H. K., Zarnegar, R. Michalopoulos, G. K. Localization of hepatocyte growth factor in human and rat tissues: an immunohistochemical study. Hepatology 1991:14488-494). In this way, in our experimental model, the impressive human uPA production modified in remaining functional hepatocytes led strongly to the in situ HGF activation which binds to its c-met receptor and induces early cell proliferation in liver, both in total parenchyma and in periportal areas (FIGS. 7A, B, C and D). Besides, it is known that HGF application in normal rat liver stimulates hepatocyte proliferation only in periportal hepatocytes (Liu, M. L. Mars, W. M., Zarnegar, R., Michalopoulos, G. K. Collagenase pretreatment and the mitogenic effects of hepatocyte growth factor and transforming growth factor-alpha in adult rat liver. Hepatology 1994: 19:1521-152 and Liu, M. L. Mars, W. M., Zarnegar, R., Michalopoulos, G. K., Uptake and distribution of hepatocyte growth factor in normal and regenerating adult rat liver. Am. J. Pathol. 1994:144:129-140), but a dramatic increase in DNA synthesis has been observed in hepatocytes of lobular areas, when normal livers were previously treated with collagenases (Liu, M. L. Mars, W. M., Zarnegar, R., Michalopoulos, G. K. Collagenase pretreatment and the mitogenic effects of hepatocyte growth factor and transforming growth factor-alpha in adult rat liver. Hepatology 1994:19:1521-152). In summary, the combined evidences presented here suggest that the active ECM degradation together with c-met increased regulation and HGF synchronous activation and binding to its corresponding receptor, activate hepatocyte proliferation. The strong proliferation response observed in cirrhotic animals injected with uPA (about 60%) could reflect the additive effect of a direct action of HGF inducible on hepatocytes and MMPs effect on hepatocyte preparation in such a way that they can offer a more effective response to growth factors (Kim, T. H., Mars, W. M., Stolz, D. B., Peterson, B. E., and Michalopoulos, G. K. Extracellular matrix remodeling at the early stages of liver regeneration in the rat. Hepatology 1997: 26:896-904).

Besides its function in plasminogen activation, it is considered that uPA is one of the main primers leading to the activation of metalloprotease cascade associated with matrix degradation (Kim, T. H., Mars, W. M., Stolz, D. B., Peterson, B. E., and Michalopoulos, G. K. Extracellular matrix remodeling at the early stages of liver regeneration in the rat. Hepatology 1997:26:896-904). After plasminogen activation into plasmin through uPA, said plasmin, in turn, activates procolagenases and possibly other metalloproteases (MMPs) to their active form, in early stages (Kim, T. H., Mars, W. M., Stolz, D. B., Peterson, B. E., and Michalopoulos, G. K. Extracellular matrix remodeling at the early stages of liver regeneration in the rat. Hepatology 1997:26:896-904). The in situ action of said enzymes brought about the ECM specific component degradation, remodeling the altered organ architecture and the appearance of newly formed blood vessels (angiogenesis) (data not shown). Even though it is clear that modified uPA overproduction activates the rapid ECM reorganization observed here, this could be regulated through mechanisms not yet elucidated, but the specific MMP-2 induction is part of said mechanisms.

Thus, besides the uPA/plasmin system initiating matrix remodeling, membrane type matrix metalloproteases (MT-MMPs) could be other inducible proteinases that have to be identified in ECM remodeling in our system, since it has been reported that MT1-MMPs could initiate pro-MMP2 activation. Thus, a collateral object of the study conducted at our laboratory is to elucidate MMPs function in huPA-induced liver fibrosis reversion.

Finally, the application of this type of strategies is being evaluated to be used on cirrhotic human beings prior determination and evaluation in animals superior to the rat. We are in the process of integrating the corresponding protocol for its evaluation in Beagle dogs and/or non-human primates.

It must be obvious for those skilled in the art that other embodiments of the present invention not shown in this description are possible and within the scope and spirit of this invention. Thus the invention is not limited to the embodiments presented in this description, and the invention is only limited by following claims and their equivalent.

The invention claimed is:

1. A recombinant adenoviral vector contained in ATCC Deposit No. PTA-10622.

2. A method of reducing collagen expression and production in liver tissue in a mammal, the method comprising intravenously administering to said mammal an effective amount of the recombinant adenoviral vector according to claim 1.

* * * * *